(12) United States Patent
Kommala et al.

(10) Patent No.: US 11,744,929 B2
(45) Date of Patent: Sep. 5, 2023

(54) PERSONALIZED RENAL FAILURE CHRONIC CARE SYSTEMS AND METHODS

(71) Applicants: Baxter International Inc., Deerfield, IL (US); BAXTER HEALTHCARE SA, Glattpark (CH)

(72) Inventors: Dheerendra R. Kommala, Lake Forest, IL (US); Rohit Nayak, Cincinnati, OH (US)

(73) Assignees: Baxter International Inc., Deerfield, IL (US); Baxter Heathcare SA, Glattpark (CH)

( * ) Notice: Subject to any disclaimer, the term of this patent is extended or adjusted under 35 U.S.C. 154(b) by 576 days.

(21) Appl. No.: 15/618,978

(22) Filed: Jun. 9, 2017

(65) Prior Publication Data

US 2018/0353670 A1 Dec. 13, 2018

(51) Int. Cl.
*G16H 20/30* (2018.01)
*G16H 20/70* (2018.01)
(Continued)

(52) U.S. Cl.
CPC .......... *A61M 1/285* (2013.01); *A61B 5/0022* (2013.01); *A61M 1/1645* (2014.02); *G16H 20/10* (2018.01); *G16H 20/30* (2018.01); *G16H 20/60* (2018.01); *G16H 20/70* (2018.01); *G16H 50/20* (2018.01); *A61M 1/1603* (2014.02); *A61M 1/287* (2013.01)

(58) Field of Classification Search
CPC .... A61M 1/285; A61M 1/1645; A61M 1/287; A61M 1/1603; G16H 20/30; G16H 20/70; G16H 20/10; G16H 50/20; G16H 20/60; A61B 5/0022; G06Q 50/20–26

See application file for complete search history.

(56) References Cited

U.S. PATENT DOCUMENTS

2005/0033133 A1* 2/2005 Kraft .................... A61B 5/0031
977/883
2006/0064037 A1* 3/2006 Shalon ................. A61B 5/0031
128/903
(Continued)

FOREIGN PATENT DOCUMENTS

WO 2011104616 9/2011
WO WO-2012038384 A1 * 3/2012 .......... A61M 1/3609
(Continued)

OTHER PUBLICATIONS

International Preliminary Reporton Patentability for application No. PCT/US2018/036661 dated Aug. 5, 2019, 2018—36 pages.
(Continued)

*Primary Examiner* — Neal Sereboff
(74) *Attorney, Agent, or Firm* — K&L Gates LLP

(57) ABSTRACT

A personalized chronic care system including (i) a sensor; (ii) a data receiving device separate from the sensor and configured to receive data directly or indirectly from the sensor; (iii) a data analytics device separate from the sensor and including at least one algorithm configured to analyze the sensor data and provide an analyzed data outcome; and (iv) at least one output device separate from the sensor and in communication with the data analytics device, the at least one output device configured to receive and communicate the analyzed data outcome to a health care provider.

23 Claims, 7 Drawing Sheets

(51) Int. Cl.
  *G16H 20/10* (2018.01)
  *G16H 50/20* (2018.01)
  *G16H 20/60* (2018.01)
  *A61M 1/28* (2006.01)
  *A61B 5/00* (2006.01)
  *A61M 1/16* (2006.01)

(56) References Cited

U.S. PATENT DOCUMENTS

| | | | |
|---|---|---|---|
| 2012/0072231 A1* | 3/2012 | Mayer | G16H 20/10 |
| | | | 705/2 |
| 2012/0203573 A1* | 8/2012 | Mayer | G16H 40/63 |
| | | | 705/3 |
| 2014/0031787 A1 | 1/2014 | Burnes et al. | |
| 2014/0288493 A1* | 9/2014 | Kamen | G16H 40/63 |
| | | | 604/66 |
| 2015/0002500 A1 | 1/2015 | Glezer et al. | |
| 2015/0149096 A1* | 5/2015 | Soykan | A61B 5/145 |
| | | | 702/19 |
| 2016/0001000 A1* | 1/2016 | Awadalla | A61M 1/1613 |
| | | | 702/19 |
| 2016/0034764 A1* | 2/2016 | Connor | G16H 20/60 |
| | | | 348/158 |
| 2017/0137885 A1* | 5/2017 | Salomon | G16H 50/20 |
| 2017/0329933 A1* | 11/2017 | Brust | G06F 16/24575 |

FOREIGN PATENT DOCUMENTS

| | | |
|---|---|---|
| WO | 2012148784 | 11/2012 |
| WO | 2016151364 | 9/2016 |

OTHER PUBLICATIONS

International Search Report for application No. PCT/US2018/036661 dated Nov. 6, 2018—8 pages.
Written Opinion of the International Searching Authority application No. PCTUS2018/036661 dated Nov. 6, 2018—21 pages.
European Office Action Appln. No. 18737073.9-1126, 3 pages dated Jan. 24, 2020.

* cited by examiner

PERSONALIZED RENAL FAILURE CHRONIC CARE SYSTEMS AND METHODS

BACKGROUND

The present disclosure relates generally to medical fluid delivery and more particularly to personalized chronic renal care.

One type of medical fluid delivery pertinent to the present disclosure is medical fluid delivery that treats kidney failure. Due to various causes, a person's renal system can fail. Renal failure produces several physiological derangements. For example, it is no longer possible to balance water and minerals or to excrete daily metabolic load. Toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that normal functioning kidneys would otherwise remove. One type of dialysis treatment is peritoneal dialysis, which infuses a dialysis solution, also called dialysis fluid, into a patient's peritoneal cavity via a catheter. The dialysis fluid contacts the peritoneal membrane of the peritoneal cavity. Waste, toxins and excess water pass from the patient's bloodstream, through the peritoneal membrane and into the dialysis fluid due to diffusion and osmosis, i.e., an osmotic gradient occurs across the membrane. An osmotic agent in dialysis provides the osmotic gradient. The used or spent dialysis fluid is drained from the patient, removing waste, toxins and excess water from the patient. This cycle is repeated multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysate fluid to drain from the peritoneal cavity. The patient then connects the catheter to a bag of fresh dialysis fluid to infuse fresh dialysis fluid through the catheter and into the patient. The patient disconnects the catheter from the fresh dialysis fluid bag and allows the dialysis fluid to dwell within the peritoneal cavity, wherein the transfer of waste, toxins and excess water takes place. After a dwell period, the patient repeats the manual dialysis procedure, for example, four times per day, each treatment lasting about an hour.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to perform the treatment cycles manually and from having to transport supplies during the day. APD machines connect fluidly to an implanted catheter, to a source or bag of fresh dialysis fluid, to a fluid drain. APD machines pump fresh dialysis fluid from a dialysis fluid source, through the catheter and into the patient's peritoneal cavity. APD machines also allow for the dialysis fluid to dwell within the cavity and for the transfer of waste, toxins and excess water to take place. The source may include multiple sterile dialysis fluid bags.

APD machines pump used or spent dialysate from the peritoneal cavity, though the catheter, to the drain. As with the manual process, several drain, fill and dwell cycles occur during APD. A "last fill" may occur at the end of APD and remains in the peritoneal cavity of the patient until the next treatment. The dialysis fluid is typically "cycled" (filled, dwelled and drained) four to five times over a treatment, e.g., nightly treatment. Typical fill volumes vary due to several clinical factors but may average about 2.0 to 2.5 liters.

In any of the above PD modalities, there are many factors to consider in providing an overall effective renal failure treatment regime besides the treatment itself. The factors include, for example, patient access for treatment, proper diagnosis, comorbidities management, getting patients out of the hospital or clinic, treatment compliance, monitoring/ management of dialysis, managing treatment cost, patient engagement, patient empowerment, and overall quality of life.

A need exists for an overall renal failure treatment regime that attempts to take into account at least some of the above-identified factors.

SUMMARY

The present disclosure sets forth systems, apparatuses and methods providing an overall renal failure treatment regime that attempts to (i) identify people whose activities and related clinical and physiological data indicate that they are at-risk for chronic kidney disease ("CKD"), (ii) provide such people with pre-CKD education and prevention efforts, (iii) monitor the health and therapy-adherence of CKD dialysis patients currently undergoing treatment, (iv) slow the progression of end-stage renal disease, and (v) monitor, manage and report on CKD patients in its various stages to enhance the medical standard of care, identify positive or negative therapy trends, and advance new treatment protocols, techniques and methodologies.

Each of (i) to (v) above involves the use of sensors, the collection of data from such sensors, the analysis of collected data to look for specified parameters, and the communication of the outcome of the analysis to the patient and/or caregiver. In one example, existing CKD patients are provided with at least one of a leg sensor and a wristband sensor. The leg sensor may for example identify nocturnal leg movement. The leg sensor or the wrist sensor may also detect autonomic variables, such as heart rate and blood pressure. The wrist sensor may also monitor the patient's sleep patterns, including sleep timings and sleep cycles. Data collected from the sensors is transmitted to one or more software algorithm that analyzes the data to look for certain results. For example, leg sensor nocturnal movement data may be used to determine if a patient has restless leg syndrome. If so, the patient and/or a health care provider ("HCP") may be notified automatically. The HCP may then order a ferritin level blood test and possibly prescribe a treatment, such as an iron therapy.

In another example, blood pressure data monitored during the night is used to look at the patient's nocturnal blood pressure dip. If the blood pressure dip decreases, the HCP may be notified automatically to determine if the patient's anti-hypertensive therapy should be titrated.

In a further example, blood pressure data monitored may also be used to determine if autonomic data suggests high sympathetic tone. If so, the HCP may be notified automatically to perhaps modify the patient's blood pressure medicine.

Volume status examples concerning existing patients with ESRD include providing the patient with a wristband sensor, for example, which measures B-type natriuretic peptide ("BNP"), heart rate ("HR"), cardiac output ("CO") and/or stroke volume ("SV"). The sensor may also be configured to collect bioimpedance data and/or blood pressure. Data collected from the sensors is transmitted to software that analyzes the data to look for certain results. For example, the BNP or bioimpedance data may be analyzed to gauge the patient's intravascular volume, and if needed, a HCP may be notified automatically to adjust the patient's diuretic and/or schedule an emergency room visit. In another volume status example, BNP or bioimpedance data may be analyzed to gauge the patient's total body water, and if needed, a HCP may be notified automatically to again adjust the patient's diuretic and/or schedule an emergency room visit. In a further body status example, HR, CO and/or SV data may be analyzed to evaluate the patient's cardiac status, and if needed, the patient's medication ("ACE") may be changed and/or schedule an emergency room visit.

Nutrition status examples concerning existing patients with ESRD include providing the patient with a wristband sensor for measuring basal metabolic rate and/or assess the patient's physical activity. Alternatively or additionally, a camera may be provided, which is used to take photographs of the patient's meals. The basal metabolic rate data may be analyzed to gauge the patient's nutritional status, such as whether the patient has a low nitrogen balance, and if needed, an HCP may be notified automatically to prompt the patient to increase protein intake with physical activity. In another example, data from the camera may be analyzed to assess the patient's caloric intake, and if needed, an HCP may be notified automatically to prompt the patient to modify his or her diet to reduce calories. Data from the camera may be used alternatively or additionally to analyze the constituents of the patient's diet to identify constituents consumed, such as sodium (NA) and phosphorous (P).

It should be appreciated that each of the above examples involves at least one sensor (which may or may not be non-invasive), a data receiving device, a data analytics device (which may or may not be the same as the data receiving device), and a data output device (which may or may not be the same as the data receiving and/or data analytics device). The data receiving device may for example be the patient's smartphone or computer that runs a program or application. The smartphone or computer may communicate wired or wirelessly with the sensor. If the output of the sensor is not compatible for direct communication with the smartphone or computer, it is contemplated to provide an intermediate input/output device, which converts the sensor signal into a format readable by the smartphone or computer. For example, the sensor may output a 4 to 20 mA or 0 to 5 VDS signal that varies depending upon what the sensor is sensing. The intermediate input/output device receives the 4 to 20 mA or 0 to 5 VDS signal and converts the signal into a format readable by the smartphone or computer, e.g., via a wireless format.

The data analytics device may for example be a server computer, e.g., cloud server computer, which is in constant or periodic communication with the smartphone or computer. The server computer includes or stores one or more algorithm that analyzes the sensor data to determine the patient's status regarding such data. To this end, the server computer may store multiple day's worth, week's worth, month's worth, or year's worth of sensor data for the patient. The algorithm that is used to evaluate the data may therefore make comparisons against limits that are standard for multiple patients, against limits that are based upon patient historical data, and/or combinations thereof. The data analytics device is in various embodiments configured to receive and analyze sensor data for multiple patients. The data analytics device may also be configured to receive and analyze data for multiple sensors for the same patient.

In an embodiment, the data analytics device outputs to multiple output devices for the same patient sensor. For example, a first output device is maintained by the HCP, so that the HCP may be informed both on a regular basis and when the patient needs medical attention. The output device for the HCP may be the HCP's smartphone or computer. The HCP's smartphone or computer may receive the output data itself, e.g., in the form of an encrypted message, or for data security reasons, may receive a patient code and an indication to visit a website (second data output device) where specific information may be viewed for the patient. A third data output device may be the software application stored at the data receiving device, for example, the patient's smartphone or computer, which along with or instead of the HCP, receives output data at the software application stored on the smartphone or computer.

A fourth data output device may be the sensor itself. The sensor may read out to the patient any of the following: (i) data sensed by the sensor (so not analyzed), (ii) output data directly from the analytics device after analyzing the sensor data, (iii) output data from the analytics device via the patient's smartphone or computer after analyzing the sensor data, (iv) reminder data directly from the analytics device to remind the patient to take some action, (v) reminder data directly from the patient's smartphone or computer to remind the patient to take some action, and (vi) reminder data from the sensor itself. Any of the above read-outs may be visual, audio, or audio/visual.

Output data to the HCP may be or include a recommendation. The recommendation may, for example, be to have the patient's medical prescription reviewed or to consider having the patient come for a medical evaluation. In one embodiment, it is then the HCP's decision concerning the best way to follow-up on the recommendation.

The systems of the present disclosure further include a medical fluid delivery machine, which may for example provide a treatment for: plasmapherisis, hemodialysis ("HD"), hemofiltration ("HF") hemodiafiltration ("HDF"), continuous renal replacement therapy ("CRRT"), apheresis, autotransfusion, hemofiltration for sepsis, and extracorporeal membrane oxygenation ("ECMO"). The systems and methods described herein may also be applicable to peritoneal dialysis ("PD") and to intravenous drug delivery. The medical fluid delivery machine is in various embodiments in wired or wireless data communication with at least one of (i) a patient's smartphone or computer for sending and receiving data two ways and/or (ii) a server computer and associated network for sending and receiving data two ways.

The systems of the present disclosure in various embodiments employ learning methods to help the patient and to build databases to streamline the methods. One learning method operated at the system of the present disclosure is configured to help people who have properly functioning kidneys but show one or more risk factor for developing kidney disease, people who have properly functioning kidneys but show early signs of kidney disease, or for patient's who have mild loss of kidney function. One goal for any of these situations is to stem further development of kidney disease or loss of kidney function. As explained in detail below, a glomerular filtration rate ("GFR") test is a blood test used to evaluate a patient's kidney function, while an albumin-to-creatinine ratio ("ACR") test is used to evaluate whether the patient has kidney disease. Either one or both of the GFR test and the ACR test is used with the learning method to determine if modifying a control variable produces positive results for the patient. The control variable may be (i) nutrition based, e.g., reduce phosphorous or sodium, (ii) lifestyle based, e.g., exercise more frequently or get more rest, or (iii) medicinally based, e.g., take blood pressure reducing medicine.

In initial steps, the patient performs a baseline ACR and/or GFR test and a list of the different control variables to test is determined. Then a first one of the control variables is selected for implementation. The selected control variable is then implemented over a suitable period of time, e.g., a few weeks to a month. During implementation, the patient enters into his or her smartphone or personal computer information indicating that the patient is complying with the control variable modification. The compliance entries may be satisfied or augmented via data from relevant sensors, such as cameras, weight scales, blood pressure monitors, etc. When control variable modification is completed, a determination is made whether the level of patient compliance has been sufficient. If not, the selected control variable is tested again. If so, then the patient undergoes a subsequent ACR and/or GFR test.

In an embodiment, the learning method determines if the particular control variable needs to undergo one or more additional trial for repeatability. If so, the one or more additional trial for the particular control variable is repeated. If not, or if all trials have been completed, then the results of the subsequent ACR and/or GFR test (or combination of multiple subsequent tests) are compared with the baseline ACR and/or GFR test results to determine if the patient's kidney disease and/or kidney functioning have worsened. If so, then the particular control variable is not added to an overall kidney maintenance plan. But if the patient's kidney disease and/or kidney functioning have stayed the same or improved, the particular control variable is added to the overall kidney maintenance plan.

The learning method next determines if there is another control variable on the list to test. If so, the above procedure is repeated for the next control variable. If not, then the overall kidney maintenance plan is formed and thereafter implemented on the patient's smartphone or personal computer. In one embodiment, the overall kidney maintenance plan, with or without specific and/or general patient data, is sent to a server and associated network, which analyzes multiple overall kidney maintenance plans together to look for trends regarding preferred control variables that consistently show an ability to maintain or improve kidney disease and/or kidney functioning levels. Such variables may then be used initially to help form the list of control variables to be tested, streamlining the learning method of the present disclosure. The learning method is also adaptable to receive and implement new control variables as they are developed. The patient's overall kidney maintenance plan may accordingly be updated as new effective control variables are determined. The first learning method accordingly learns and advances in multiple, different ways.

Another learning method contemplated for the systems of the present disclosure involves patients that are further along the kidney disease and kidney function reduction path, and who are currently being treated by a dialysis machine. Here, the goal of the learning method is in one embodiment to reduce the effects or the likelihood of the onset of common co-morbidity factors, including heart disease, stroke and diabetes. In an embodiment, the method includes the selection of a goal, e.g., to minimize patient volume (leading to heart disease), blood pressure (leading to heart disease or stroke), or blood sugar (leading to diabetes). The patient may enter into the patient's smartphone or computer one of the above goals. The patient, e.g., in cooperation with a doctor or clinician, develops a list of controllable variables selected to determine their effect, if any, on the selected goal. For example, controllable variables for patient volume include limiting the weight of food and/or liquid consumed per day to a certain amount, or regulating the amount of food and/or liquid consumed after treatment, so that a greater percentage of food and/or liquid is consumed, e.g., closer to (or farther from) the next dialysis treatment. Controllable variables for patient blood pressure may include limiting sodium intake, limiting fatty foods, and limiting alcohol intake. Controllable variables for patient blood sugar include limiting sugar intake and limiting dextrose or glucose levels in peritoneal dialysis fluids.

Once the list of controllable variables for the selected co-morbidity goal is entered into the patient's smartphone or computer, a control variable is selected to analyze. Afterwards, the selected control variable is modified by the patient over a suitable time period, e.g., twenty days or a month. During this time, the patient enters compliance confirmations into a smartphone or computer at a desired interval, e.g., daily. For patient volume for example, once every day, the patient may confirm at that the patient has consumed less than a weight limit of food and/or liquid. For patient blood pressure, the patient may confirm that the patient has consumed less than a prescribed limit of sodium. For patient blood sugar, the patient may confirm that the patient has consumed less than a prescribed limit of dextrose or glucose.

Sensors may be used to verify the patient's compliance entry. Sensors are also used for evaluation and send evaluation data to the patient's smartphone or computer, which data may in turn be sent to a server and network for dissemination to a website at clinician's smartphone or computer. For the goal of patient volume, patient weight data via a weigh scale is delivered on a periodic basis, including patient weight before and after each dialysis treatment. For the goal of patient blood pressure, patient blood pressure data via a blood pressure monitor is delivered on a periodic basis, including patient blood pressure before and after each dialysis treatment. For the goal of patient blood sugar, patient blood sugar data via a glucose monitor is delivered on a periodic basis, including patient blood sugar before and after each dialysis treatment.

When the control variable modification has been completed, it may be determined whether a compliance threshold has been met. The compliance threshold may be different for different control variables and different co-morbidity goals. If the compliance threshold has not been met, the testing for the same control variable is repeated. If the compliance threshold for the current control variable has been met, method evaluates the evaluation data sent from evaluation sensors. The evaluation in one embodiment determines a deviation from a desired or expected value. For patient volume, one deviation evaluation includes determining how far the patient's actual weight is from the patient's dry weight just before treatment, where less water to remove is better. For patient blood pressure, for example, the deviation evaluation may determine how far off the patient's blood pressure is on average over the evaluation period (including during treatments) from a desired blood pressure for the patient. For patient blood sugar, for example, the deviation evaluation may determine how far off the patient's blood sugar level is on average over the evaluation period (including during treatments) from a desired blood sugar level.

After evaluation, the method may determine whether another trial for the same control variable should be performed. Certain control variables may only warrant a single trial, while other control variables may warrant two or more trials for repeatability. If another trial for the current control variable exists, then the above steps are repeated. When there is no additional trial, the method determines whether the deviation evaluation result, or combined deviation evaluation results from multiple trials, indicate(s) that the particular co-morbidity goal is being aided or assisted. If not, then the current control variable for patient is determined not to be part of the patient's overall kidney treatment plan for the selected co-morbidity goal. If the deviation evaluation result, or the combined deviation evaluation results from multiple trials, instead indicate(s) that the co-morbidity goal is being aided or assisted, then the current control variable is determined to be part of the patient's overall kidney maintenance plan for the selected co-morbidity goal.

The method may then determine whether another control variable for the selected co-morbidity goal is set for analysis. If another control variable for the selected co-morbidity goal exists, then the above steps are repeated for another control variable. When there is no additional control variable to analyze, the method combines all control variables determined to be part of the patient's overall kidney maintenance plan to form the plan for the selected co-morbidity goal. The patient's smartphone or computer thereafter implements, monitors and controls the overall kidney maintenance plan. The patient's smartphone or computer may also upload the overall kidney maintenance plan to the server and network. One or more algorithm at the server may be programmed to combine multiple overall kidney maintenance plans to look for trends and identify which control variables, and possibly which combinations of control variables, appear to be most effective.

The above second learning method may then be repeated at the present system for another co-morbidity goal, such as any of the remaining ones of (i) regulating patient volume, (ii) regulating blood pressure, or (iii) regulating blood sugar. The second learning method is also adaptable to receive and implement new co-morbidity goals and/or control variables for one or more co-morbidly goal as they are developed. The patient's overall kidney maintenance plan may accordingly be updated as new effective control variables are determined. The second learning method learns and advances in multiple, different ways.

In light of the disclosure herein and without limiting the disclosure in any way, in a first aspect of the present disclosure, which may be combined with any other aspect listed herein unless specified otherwise, a personalized renal failure chronic care system for a patient includes: a patient data input and output device; a server operating over a network; a health care provider ("HCP") data input and output device in communication with the server via the network; software stored on the patient data input and output device, the server, or the HCP data input and output device, the software presenting a plurality of controllable variables for selection, wherein a selected controllable variable is scheduled to be modified over a testing period; a compliance entry feature configured to confirm that the controllable variable is modified over the testing period as scheduled; an evaluation performed by the software to determine whether the selected controllable variable is to be included in an overall kidney maintenance plan; and wherein the overall kidney maintenance plan is implemented by the patient data input and output device, the overall kidney maintenance plan including at least one approved controllable variable.

In a second aspect of the present disclosure, which may be combined with any other aspect listed herein unless specified otherwise, the software is configured to slow or stop the spread of kidney disease or loss of kidney function, and wherein the evaluation includes determining how the selected controllable variable affects at least one of an albumin-to-creatinine ratio ("ACR") test or a glomerular filtration rate ("GFR") test performed on the patient.

In a third aspect of the present disclosure, which may be combined with the second aspect in combination with any other aspect listed herein unless specified otherwise, wherein the evaluation results in the selected controllable variable being included in the overall kidney maintenance plan if the at least one ACR or GFR test does not show worsening of kidney disease or loss of kidney function.

In a fourth aspect of the present disclosure, which may be combined with the second aspect in combination with any other aspect listed herein unless specified otherwise, the controllable variables for selection include at least one nutritional variable, lifestyle variable, or medicinal variable.

In a fifth aspect of the present disclosure, which may be combined with the fourth aspect in combination with any other aspect listed herein unless specified otherwise, the nutritional variable includes at least one of (i) phosphorous to be reduced in the patient's diet, (ii) calcium to be reduced in the patient's diet, (iii) sodium to be reduced in the patient's diet, (iv) alcohol consumption to be reduced, (v) water to be consumed in a prescribed amount, (vi) an antioxidant to be consumed in a prescribed amount, (vii) sugar consumption to be reduced, or (viii) a vitamin consumed in a prescribed amount.

In a sixth aspect of the present disclosure, which may be combined with the fourth aspect in combination with any other aspect listed herein unless specified otherwise, the lifestyle variable includes at least one of (i) going to sleep by a prescribed hour in a day, (ii) performing a certain amount of exercise, or (iii) eliminating food consumption after a certain time in a day.

In a seventh aspect of the present disclosure, which may be combined with the fourth aspect in combination with any other aspect listed herein unless specified otherwise, the medicinal variable includes at least one of a blood pressure reducing drug or an appetite suppressing drug.

In an eighth aspect of the present disclosure, which may be combined with the second aspect in combination with any other aspect listed herein unless specified otherwise, the personalized renal failure chronic care system includes at least one sensor in data communication with the patient data input and output device and having an output used for or in combination with confirmation by the patient that the controllable variable is modified over the testing period as scheduled.

In a ninth aspect of the present disclosure, which may be combined with the eighth aspect in combination with any other aspect listed herein unless specified otherwise, the at least one sensor includes (i) a heart rate monitor, (ii) a camera producing a timestamped photograph of the patient's food, or (iii) a blood pressure monitor.

In a tenth aspect of the present disclosure, which may be combined with any other aspect listed herein unless specified otherwise, the software is configured to slow or stop a co-morbidity factor affected by the controllable variable, and wherein the evaluation includes determining an effect of the controllable variable on the co-morbidity factor relative to a desired value for the co-morbidity factor.

In an eleventh aspect of the present disclosure, which may be combined with the tenth aspect in combination with any other aspect listed herein unless specified otherwise, a first co-morbidity factor is patient volume leading to heart failure, a second co-morbidity factor is patient blood pressure leading to heart failure or stroke, and a third co-morbidity factor is patient blood sugar leading to diabetes.

In a twelfth aspect of the present disclosure, which may be combined with the tenth aspect in combination with any other aspect listed herein unless specified otherwise, the plurality of controllable variables for selection are associated with a co-morbidity factor selected from a plurality of co-morbidity factors.

In a thirteenth aspect of the present disclosure, which may be combined with the twelfth aspect in combination with any other aspect listed herein unless specified otherwise, the selected co-morbidity factor is patient volume and the associated controllable variables include at least one of (i) weight of food consumed being limited, (ii) weight of liquid consumed being limited, (iii) weight of food and liquid consumed being limited, or (iv) amount of food and/or liquid consumed after treatment regulated so that a greater percentage of food and/or liquid is consumed closer to or farther from a next dialysis treatment.

In a fourteenth aspect of the present disclosure, which may be combined with the twelfth aspect in combination with any other aspect listed herein unless specified otherwise, the selected co-morbidity factor is patient blood pressure and the associated controllable variables include at least one of (i) sodium intake being limited, (ii) sodium level of dialysis fluid used during treatment being limited, (iii) fatty foods being limited, or (iv) alcohol consumed being limited.

In a fifteenth aspect of the present disclosure, which may be combined with the twelfth aspect in combination with any other aspect listed herein unless specified otherwise, the selected co-morbidity factor is patient blood sugar and the associated controllable variables include at least one of (i) sugar intake being limited and (ii) dextrose or glucose levels in peritoneal dialysis fluid being limited.

In a sixteenth aspect of the present disclosure, which may be combined with the tenth aspect in combination with any other aspect listed herein unless specified otherwise, a first sensor is used with the compliance entry feature to confirm that the controllable variable is modified over the testing period as scheduled and a second sensor is used for the evaluation to determine the effect of the controllable variable on the co-morbidity factor relative to the desired value for the co-morbidity factor.

In a seventeenth aspect of the present disclosure, which may be combined with the sixteenth aspect in combination with any other aspect listed herein unless specified otherwise, the co-morbidity factor is patient volume, the first sensor includes a weigh scale for food and/or water consumed, and the second sensor includes a weigh scale for weighing the patient.

In an eighteenth aspect of the present disclosure, which may be combined with the sixteenth aspect in combination with any other aspect listed herein unless specified otherwise, the co-morbidity factor is patient blood pressure, the first sensor includes a camera for reading sodium levels, and the second sensor includes a blood pressure monitor.

In a nineteenth aspect of the present disclosure, which may be combined with the sixteenth aspect in combination with any other aspect listed herein unless specified otherwise, the co-morbidity factor is patient blood sugar, the first sensor includes a camera for reading dextrose or glucose levels, and the second sensor includes a glucose meter.

In a twentieth aspect of the present disclosure, which may be combined with any other aspect listed herein unless specified otherwise, the software is configured to perform the evaluation only if a level of compliance from the compliance entry feature meets a threshold level.

In a twenty-first aspect of the present disclosure, which may be combined with any other aspect listed herein unless specified otherwise, wherein the overall kidney maintenance plan is analyzed at the server or the HCP data input and output device with at least one other overall kidney maintenance plan to establish at least one preferred controllable variable.

In a twenty-second aspect of the present disclosure, which may be combined with any other aspect listed herein unless specified otherwise, at least one of (i) the patient data input and output device includes a smartphone or a personal computer, (ii) the HCP data input and output device includes a smartphone or a personal computer, or (iii) the compliance entry feature includes a compliance entry screen displayed by (a) the patient data input and output device, (a) the HCP data input and output device, or (c) a website provided via the network, (iv) the overall kidney maintenance plan is implemented by the patient using the patient data input and output device, or (v) the overall kidney maintenance plan is determined at the patient input and output device and delivered to the server or the HCP data input and output device.

In a twenty-third aspect of the present disclosure, which may be combined with any other aspect listed herein unless specified otherwise, a personalized renal failure chronic care system operating with a sensor providing sensor data including at least one of blood pressure data, glucose data or nutritional data for a patient, the system including: a data analytics device separate from the sensor and including at least one algorithm configured to analyze the sensor data and provide an analyzed data outcome, the analyzed data outcome useful in assessing a potential or current renal failure patient, wherein at least one of (i) the at least one algorithm analyzes the blood pressure data and the analyzed data outcome includes at least one blood pressure lowering recommendation particular to the patient, (ii) the at least one algorithm analyzes the glucose data and the analyzed data outcome includes at least one glucose lowering recommendation particular to the patient, or (iii) the at least one algorithm analyzes the nutritional data and the analyzed data outcome includes at least one nutritional recommendation particular to the patient.

In a twenty-fourth aspect of the present disclosure, which may be combined with the twenty-third aspect in combination with any other aspect listed herein unless specified otherwise, the data analytics device is configured to communicate with a data receiving device configured to receive data directly or indirectly from the sensor.

In a twenty-fifth aspect of the present disclosure, which may be combined with the twenty-third aspect in combination with any other aspect listed herein unless specified otherwise, the data analytics device is configured to communicate with at least one output device configured to receive and communicate the analyzed data outcome to the patient and/or a health care provider.

In a twenty-sixth aspect of the present disclosure, which may be combined with the twenty-third aspect in combination with any other aspect listed herein unless specified otherwise, the blood pressure lowering recommendation includes a sodium intake limit or reduction technique.

In a twenty-seventh aspect of the present disclosure, which may be combined with the twenty-third aspect in combination with any other aspect listed herein unless specified otherwise, the glucose lowering recommendation includes a glucose limit or glucose reduction technique.

In a twenty-eighth aspect of the present disclosure, which may be combined with the twenty-third aspect in combination with any other aspect listed herein unless specified otherwise, the nutritional recommendation includes a caloric intake limit, a vitamin recommendation, or a food intake recommendation.

In a twenty-ninth aspect of the present disclosure, which may be combined with any other aspect listed herein unless specified otherwise, a personalized renal failure chronic care system includes: a sensor; a data receiving device separate from the sensor and configured to receive data directly or indirectly from the sensor for a patient; a data analytics device separate from the sensor and including at least one algorithm configured to analyze the sensor data and provide an analyzed data outcome particular to the patient, the analyzed data outcome useful in assessing a potential or current renal failure patient; and at least one output device in communication with the data analytics device, the at least one output device configured to receive and communicate the analyzed data outcome to the patient and/or a health care provider.

In a thirtieth aspect of the present disclosure, which may be combined with the twenty-ninth aspect in combination with any other aspect listed herein unless specified otherwise, the sensor is invasive, noninvasive or minimally invasive.

In a thirty-first aspect of the present disclosure, which may be combined with the twenty-ninth aspect in combination with any other aspect listed herein unless specified otherwise, the sensor is at least one of: a wristband sensor, a leg sensor, a camera, a heartrate sensor, a blood pressure sensor, a glucose sensor, a weight sensor, or a temperature sensor.

In a thirty-second aspect of the present disclosure, which may be combined with the twenty-ninth aspect in combination with any other aspect listed herein unless specified otherwise, the data receiving device includes a patient smartphone or a patient computer.

In a thirty-third aspect of the present disclosure, which may be combined with the twenty-ninth aspect in combination with any other aspect listed herein unless specified otherwise, the data analytics device includes a server.

In a thirty-fourth aspect of the present disclosure, which may be combined with the twenty-ninth aspect in combination with any other aspect listed herein unless specified otherwise, the data receiving device and the data analytics device are both located at a patient's smartphone or computer.

In a thirty-fifth aspect of the present disclosure, which may be combined with the twenty-ninth aspect in combination with any other aspect listed herein unless specified otherwise, the data receiving device is in communication with the data analytics device.

In a thirty-sixth aspect of the present disclosure, which may be combined with the twenty-ninth aspect in combination with any other aspect listed herein unless specified otherwise, the at least one output device includes at least one of a patient smartphone, a patient computer, a website, or the sensor.

In a thirty-seventh aspect of the present disclosure, which may be combined with the twenty-ninth aspect in combination with any other aspect listed herein unless specified otherwise, the at least one output device includes at least one of a patient smartphone, a patient computer, or a website.

In a thirty-eighth aspect of the present disclosure, which may be combined with the twenty-ninth aspect in combination with any other aspect listed herein unless specified otherwise, the analyzed data outcome includes a renal failure recommendation.

In a thirty-ninth aspect of the present disclosure, which may be combined with the twenty-ninth aspect in combination with any other aspect listed herein unless specified otherwise, the at least one algorithm is configured to compare the sensor data to at least one limit or range to produce the analyzed data outcome.

In a fortieth aspect of the present disclosure, which may be combined with the twenty-ninth aspect in combination with any other aspect listed herein unless specified otherwise, the at least one limit or range is standardized for multiple patients.

In a forty-first aspect of the present disclosure, which may be combined with the twenty-ninth aspect in combination with any other aspect listed herein unless specified otherwise, the at least one limit or range is patient specific.

In a forty-second aspect of the present disclosure, which may be combined with the twenty-ninth aspect in combination with any other aspect listed herein unless specified otherwise, the at least one algorithm is configured to sum the sensor data to produce the analyzed data outcome.

In a forty-third aspect of the present disclosure, which may be combined with the twenty-ninth aspect in combination with any other aspect listed herein unless specified otherwise, the at least one algorithm is configured to use the sensor data in combination with at least one look-up table to produce the analyzed data outcome.

In a forty-fourth aspect of the present disclosure, which may be combined with the twenty-ninth aspect in combination with any other aspect listed herein unless specified otherwise, the sensor provides first sensed data and second, different sensed data, and wherein the data analytics device includes (i) a first algorithm configured to analyze the first sensor data and provide a first analyzed data outcome and (ii) a second algorithm configured to analyze the second sensor data and provide a second analyzed data outcome.

In a forty-fifth aspect of the present disclosure, which may be combined with the twenty-ninth aspect in combination with any other aspect listed herein unless specified otherwise, the sensor is a first sensor providing first sensed data, and which includes a second sensor for a same patient providing second, different sensed data, and wherein the data analytics device includes (i) a first algorithm configured to analyze the first sensor data and provide a first analyzed data outcome and (ii) a second algorithm configured to analyze the second sensor data and provide a second analyzed data outcome.

In a forty-sixth aspect of the present disclosure, which may be combined with the twenty-ninth aspect in combination with any other aspect listed herein unless specified otherwise, the sensor is a first sensor providing a first sensed data type, and which includes a second sensor for a different patient providing the same first sensed data type, and wherein the data analytics device includes a first algorithm configured to analyze the first sensor data type of both the first and second sensors and provide a first analyzed data outcome for the first sensor and a second analyzed data outcome for the second sensor.

In a forty-seventh aspect of the present disclosure, which may be combined with the twenty-ninth aspect in combination with any other aspect listed herein unless specified otherwise, the sensor is a first sensor providing a first sensed data, and which includes a second sensor for a different patient providing a second, different sensed data, and wherein the data analytics device includes (i) a first algorithm configured to analyze the first sensor data and provide a first analyzed data outcome and (ii) a second algorithm configured to analyze the second sensor data and provide a second analyzed data outcome.

In a forty-eighth aspect, which may be combined with any with any other aspect listed herein unless specified otherwise, a personalized renal failure chronic care system for a patient includes: a patient data input and output device; software stored on the patient data input and output device, the software presenting a plurality of controllable variables for selection, wherein a selected controllable variable is scheduled to be modified over a testing period; a compliance entry screen displayed by the patient data input and output device, the compliance entry screen configured to confirm that the controllable variable is modified over the testing period as scheduled; an evaluation performed by the software to determine whether the selected controllable variable is to be included in an overall kidney maintenance plan; and wherein the overall kidney maintenance plan is implemented by the patient data input and output device, the overall kidney maintenance plan including at least one approved controllable variable.

In a forty-ninth aspect of the present disclosure, any of the structure, functionality and alternatives discussed in connection with any one of FIGS. 1 to 7 may be combined with any of the structure, functionality and alternatives discussed in connection any other of FIGS. 1 to 7.

In light of the above discussion and aspects of the present disclosure, it is accordingly an advantage of the present disclosure to provide an improved medical system and method.

It is another advantage of the present disclosure to expand the collection of patient information, both clinical and physiological.

It is a further advantage of the present disclosure to increase the frequency of the collection of patient information, both clinical and physiological.

It is yet another advantage of the present disclosure to improve the detection of the onset of kidney disease via real world data ("RWD") methods with analytics to identify and drive automated personalized interventions for the patient using real-time, real world evidence ("RWE"), e.g., in a non-clinical setting.

It is yet a further advantage of the present disclosure to impede the progression of kidney disease via RWD methods with analytics to identify and drive automated personalized interventions for the patient using real-time, RWE, e.g., in a non-clinical setting.

It is still another advantage of the present disclosure to aid kidney disease treatment compliance.

It is still a further advantage of the present disclosure to aid in the prevention, detection and treatment of co-morbidity diseases associated with kidney disease.

Still further, it is an advantage of the present disclosure to provide systems and methods that learn and evolve based upon evaluation and allow for new information to be added so as to provide up-to-date solutions to patients and caregivers.

The advantages discussed herein may be found in one, or some, and perhaps not all of the embodiments disclosed herein. Additional features and advantages are described herein, and will be apparent from the following Detailed Description and the figures.

DETAILED DESCRIPTION

Figure 1:
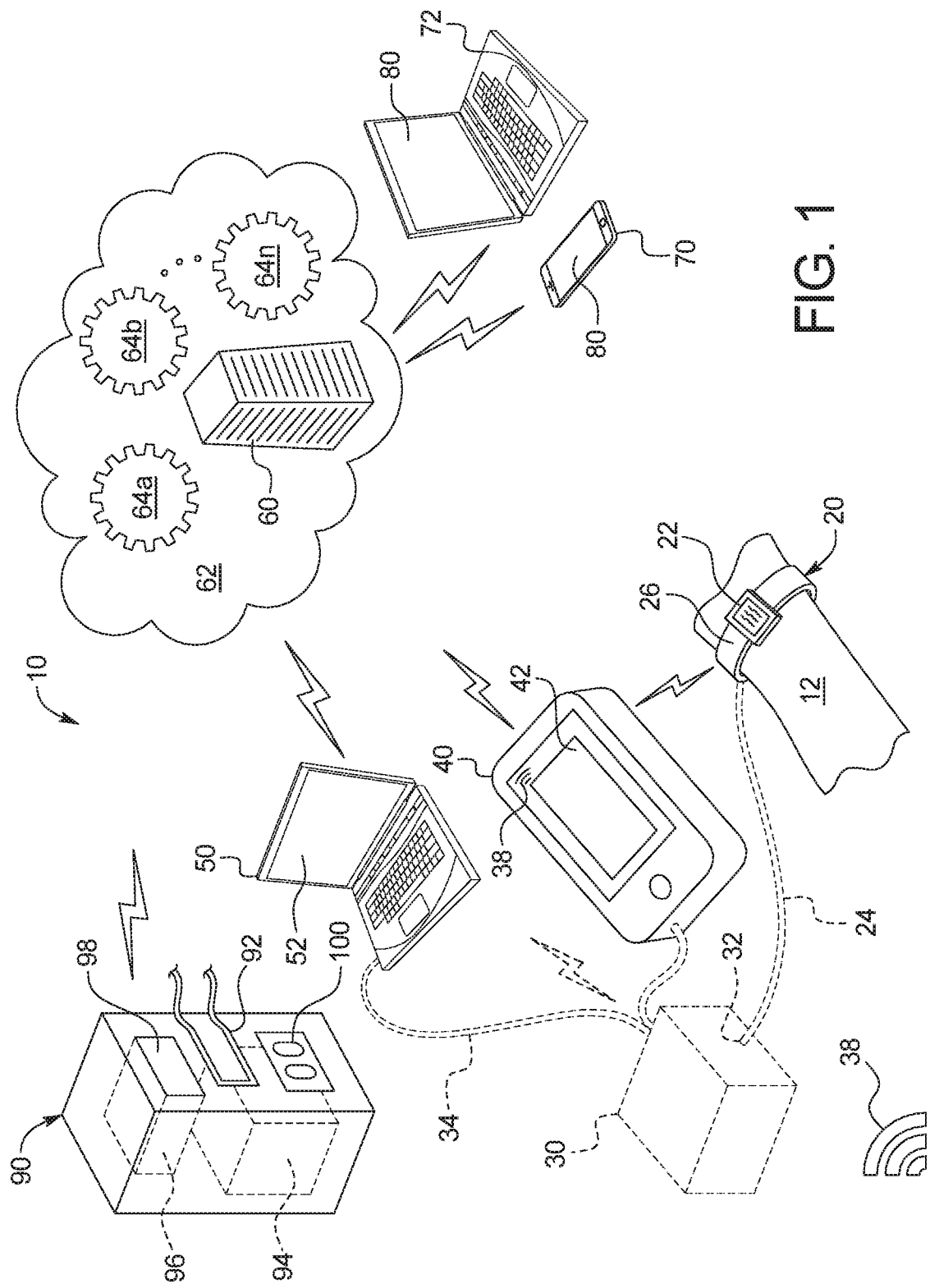
FIG. 1 is a schematic view of one embodiment of a personalized chronic, e.g., renal, care system of the present disclosure.

Referring now to the drawings and in particular to FIG. 1, an embodiment of a personalized chronic, e.g., renal, care system and associated method of the present disclosure for a patient, such as a dialysis patient 12, is illustrated by system 10. System 10 includes a sensor 20. Sensor 20 may be invasive, non-invasive or minimally invasive as needed. Sensor 20 in FIG. 1 is a non-invasive wristband sensor, which may for example, track any one or more of patient movement, heartrate, and sleep patterns, for example. Sensor 20 includes a display 22, such as a liquid crystal display ("LCD") or a light emitting ("LED") display. Sensor 20 outputs sensed data wirelessly 30 or optionally (shown in dashed line) via hardwire 24. Sensor 20 may also include a port 26 for receiving a power cord (not illustrated) to charge a rechargeable battery provided with sensor 20. Sensor 20 may output sensed data intermittently, semi-continuously or continuously. Sensor 20 may be a blood pressure cuff or other type of blood pressure sensor, leg sensor, camera, heartrate sensor, glucose sensor, weight sensor, conductivity sensor, temperature sensor, analyte sensor, composition sensor, and combinations thereof. Sensor 20 may provide its own electronic output. In alternative embodiments, sensor 20 may provide a visual output, e.g., a litmus type output, which patient 12 converts to a number and enters into his or her smartphone 40 or computer 50. Sensor 20 may be provided along with a patient fluid transfer set, such as a blood tubing set, to sense a parameter of a patient fluid, e.g., blood, saliva, used dialysis fluid, and the like.

Sensed data is sent to a data receiving device, which may for example be the patient's smartphone 40 or computer 50. Smartphone 40 runs a program or application 42 that accepts the sensed data, while computer 50 runs a program or application 52 that accepts the sensed data. Smartphone 40 or computer 50 may communicate wired or wirelessly and directly with sensor 20 if the sensed data is in a form readable by applications 42 and 52. If the sensed data output of sensor 20 is not compatible for direct communication with smartphone 40 or computer 50, it is contemplated to provide an intermediate input/output device 30, which converts the sensor signal into a format readable by smartphone 40 or computer 50. For example, sensor 20 may output a 4 to 20 mA or 0 to 5 VDS signal that varies depending upon what sensor 20 is sensing. Intermediate input/output device 30 receives the 4 to 20 mA or 0 to 5 VDS signal and converts the signal into a format readable by smartphone 40 or computer 50, e.g., via a wireless format. In an alternative embodiment (not illustrated), intermediate input/output device 30 is in wired communication with smartphone 40 or computer 50.

Because intermediate input/output device 30 is optional, or used only if sensed data may not be sent directly to smartphone 40 or computer 50, it is shown in dashed line. Nevertheless, intermediate input/output device 30 may include an inlet 32 for receiving hardwire 24 from sensor 20 and an outlet, not seen in FIG. 1, for receiving hardwire 34 extending between intermediate input/output device 30 and smartphone 40 or computer 50. Hardwire 34 carries sensor data which has been converted at intermediate input/output device 30 into a form suitable for smartphone 40 or computer 50 to one those devices. In an alternative embodiment, sensor data which has been converted at intermediate input/output device 30 into a form suitable for smartphone 40 or computer 50 may be sent wirelessly between intermediate input/output device 30 and smartphone 40 and/or computer 50.

As illustrated in FIG. 1, sensor 20, optional input/output device 30, smartphone 40 and computer 50 operate in a wireless environment 38 in one embodiment. Communication for wireless environment 38 may be via any of Bluetooth™, WiFi™, Zigbee®, Z-Wave®, wireless Universal Serial Bus ("USB"), infrared, or any other suitable wireless communication technology.

Software programs or applications 42 and 52 store sensor data for at least as long as it is needed to relay the sensor data to a data analytics device or server 60. In one embodiment, software programs or applications 42 and 52 stream sensor data to data analytics device or server 60 when it is received at software programs or applications 42 and 52. In such a case, software programs or applications 42 and 52 do not need to store sensor data for a long period and may write over stored data on some cyclic frequency. In another embodiment, data analytics device or server 60 calls for software programs or applications 42 and 52 to deliver data to the data analytics device or server 60 on some convenient time schedule, e.g., once every few minutes, once every hour, once every few hours, or once every day. Here, software programs or applications 42 and 52 store sensor data for at least as long as needed to meet the next data call by data analytics device or server 60. In a further alternative embodiment, software programs or applications 42 and 52 store sensor data for a designated period of time before calling data analytics device or server 60 to deliver data to the data analytics device or server 60. The designated period of time may, for example, be once every few minutes, once every hour, once every few hours, or once every day. Here, software programs or applications 42 and 52 store sensor data for at least as long as the designated period of time.

It should be appreciated that each of the above embodiments for the transfer of sensor data between software programs or applications 42 and 52 and data analytics device or server 60 is equally applicable to the transfer of sensor data between sensor 20 and software programs or applications 42 and 52. Sensor 20 may therefore have processing and memory configured to hold sensed data for as long as needed. The type of sensor may dictate how and when data is transferred. For example, a heartrate sensor may generate data on a continuous or semi-continuous basis and therefore generate a lot of data. Here, it may be more convenient to bundle the data and deliver it in bulk to the software programs or applications 42 and 52 and/or to the data analytics device or server 60. Such bulk data may be time stamped by sensor 20, e.g., including date and time period, e.g., 2:00 PM to 4:00 PM. Other types of sensors are only used periodically and generate only a single or few pieces of data, e.g., patient weigh scales, glucose sensors, and calorie counters. Here, it may be more convenient to deliver the sensor data as it is generated to the software programs or applications 42 and 52 and/or to the data analytics device or server 60. Such instantaneous data may be time stamped by sensor 20, e.g., including date and time taken. It is accordingly contemplated that system 10 may deliver data between sensors 20, software programs or applications 42 and 52 and data analytics device or server 60 differently based upon the type of sensor.

Server 60 in the illustrated embodiment operates in a cloud environment 62 and stores multiple algorithms 64a, 64b . . . 64n. Different algorithms 64a, 64b . . . 64n may be stored for the same sensor 20. For example, sensor 20 in FIG. 1 may measure movement, heartrate, and sleep patterns, wherein algorithm 64a is provided to analyze patient movement data, algorithm 64b is provided to analyze patient heartrate data, and algorithm 64c is provided to analyze patient sleep pattern data. Different algorithms 64a, 64b . . . 64n may alternatively or additionally be stored to analyze data from different types of sensors 20. For example, algorithm 64a may be provided to analyze data from a patient blood pressure sensor, algorithm 64b may be provided to analyze data from a patient weigh scale, while algorithm 64c is provided to analyze data from a patient glucose sensor.

Algorithms 64a, 64b . . . 64n in certain embodiments operate by comparing recent sensor data to one or more limit for that sensor data. For example, patient blood pressure data may be compared to upper and lower blood pressure limits. The limits may be standardized for all patients or be tailored for each specific patient. It is contemplated to log sensor data over time for each patient at analytics device or server 60. The data may be averaged or trended to develop static or shifting limits specific to the patient. Patient weight is a good example of sensed data that is better analyzed against patient-specific limits rather than against standardized patient limits. Blood pressure is an example of sensed data that may be compared against patient-specific limits and standardized limits. For example, narrower upper and lower patient- specific blood pressure limits may be set around the patient's current average blood pressure known at analytics device or server 60, while wider upper and lower standard blood pressure limits may be set around the patient's current average blood pressure. If the patient's currently sensed blood pressure trips a narrower patient-specific limit, the health care provider ("HCP") may be notified to keep a watch on the patient's blood pressure, whereas if a wider standard blood pressure limit is tripped, the HCP is notified to contact the patient immediately. It is accordingly contemplated for algorithms 64a, 64b . . . 64n to set one or more standard sensed data limit, one or more patient-specific sensed data limit, and combinations thereof.

Algorithms 64a, 64b . . . 64n in certain embodiments accumulate information over time. For example, patient calorie data may be accumulated for a day, week or month and then be averaged to some desired period, e.g., calories per day. The averaged calories per day may then be compared to one or more or both of a standard limit or a patient-specific limit. Other examples of algorithms 64a, 64b . . . 64n are discussed in detail below.

In various embodiments, data analytics device or server 60 may output to multiple output devices for the same patient sensor. For example, a first output device 70, 72 is maintained by the HCP, so that the HCP may be informed both on a regular basis and when the patient needs medical attention. The output device for the HCP may be the HCP's smartphone 70 or computer 72. The HCP's smartphone 70 or computer 72 may receive the output data itself, e.g., in the form of an encrypted message, or for data security reasons, may receive a patient code and an indication to visit a website 80 (second data output device) where specific information may be viewed for the patient. One suitable website 80 is described in U.S. Publication No. 2013/0310726, entitled, "Home Medical Device Systems and Methods for Therapy Prescription and Tracking, Servicing and Inventory", filed Mar. 14, 2013, the entire contents of which are incorporated herein by reference and relied upon. A third data output device may be the software application 42 or 52 stored at the data receiving device, for example, the data receiving device may be the patient's smartphone 40 or computer 50. The patient's smartphone 40 or computer 50 may, along with or instead of HCP's smartphone 70 or computer 72, receive output data at software application 42 or 52 stored on the patient's smartphone 40 or computer 50.

A fourth data output device may be sensor 20 itself. As discussed above, sensor 20 may include a display 22 that reads out to the patient any of the following: (i) data sensed by sensor 20 (so raw, not analyzed data), (ii) output data directly from analytics device or server computer 60 after analyzing the sensor data, (iii) output data from analytics device or server computer 60 via the patient's smartphone 40 or computer 50 after analyzing the sensor data, (iv) reminder data directly from analytics device or server 60 to remind patient 12 to take some action, (v) reminder data directly from the patient's smartphone 40 or computer 50 to remind patient 12 to take some action, and (vi) reminder data from sensor 20 itself. Any of the above read-outs may be visual, audio, or audio/visual, that is, along with display 22, sensor 20 may also include a speaker and/or beeper.

Output data to HCP smartphone 70, HCP computer 72 or website 80 may be or include a recommendation. The recommendation may, for example, be to have the patient's medical prescription reviewed or to consider having the patient come for a medical evaluation. In one embodiment, it is then the HCP's decision on how to follow-up on the recommendation. Multiple example outputs to the HCP are explained in detail below.

In an alternative embodiment, data analytics device 60 including algorithms 64a, 64b . . . 64n is combined with the data receiving device at the patient's smartphone 40 or computer 50. Here, the patient's smartphone 40 or computer 50 may communicate directly with the at least one output device, e.g., at least one of HCP smartphone 70, HCP computer 72 or website 80.

FIG. 1 further illustrates that patient 12 is treated by a medical fluid delivery machine 90. Medical fluid delivery machine 90 may include, for example, a medical device to provide a treatment for: plasmapherisis, hemodialysis ("HD"), hemofiltration ("HF") hemodiafiltration ("HDF"), continuous renal replacement therapy ("CRRT"), apheresis, autotransfusion, hemofiltration for sepsis, and extracorporeal membrane oxygenation ("ECMO"). The systems and methods described herein may also be applicable to peritoneal dialysis ("PD") and to intravenous drug delivery. These modalities may be referred to collectively or generally individually as medical fluid delivery.

Moreover, each of the assemblies, machines and methods described herein may be used in clinical and/or home-based applications. For example, the assemblies may be employed in in-center HD, HF or HDF machines, which run throughout the day. Alternatively, the assemblies may be used with home HD, HF or HDF machines, which are operated at the patient's convenience. One such home HD system that may be modified according to the present disclosure is described in U.S. Pat. No. 8,029,454, entitled "High Convection Home Hemodialysis/Hemofiltration and Sorbent System", filed Nov. 4, 2004, the entire contents of which are incorporated herein by reference and relied upon.

The HD version of machine 90 may include, for example, a blood or extracorporeal circuit 92 having an arterial line that extends from an arterial needle placed in fluid communication with the blood system of patient 12. The arterial line includes a negative pressure branch that runs to a blood pump (membrane/volumetric or peristaltic) and a positive pressure branch that runs from the blood pump to a dialyzer. A venous line extends from the dialyzer to a venous needle, which is likewise placed in fluid communication with the blood system of patient 12. The venous line may include a drip chamber. One or more pressure sensor may be located to sense the pressure of the venous and/or arterial lines. An electrical or pressure/wave-based access disconnection system ("ADS") may be employed to sense the dislodgement of the venous needle and perhaps the arterial needle additionally. An occluder or other type of arterial and/or venous line clamp may be provided to clamp the blood lines in an alarm situation. Plural valves, e.g., pinch or pneumatic, may be used in combination with the blood pump. Blood or extracorporeal circuit 92 including the dialyzer may be provided as a single or multiple use disposable that is placed on and is operated by the chassis of machine 90.

The HD version of machine 90 may also include for example, a dialysis fluid circuit 94 that pumps fresh dialysis fluid to and used dialysis fluid from the dialyzer. Pumping may be achieved via membrane/volumetric pumps, peristaltic pumps or gear pumps. The dialysis fluid pumps may operate with balance chambers, known in the art, for metering a like fresh dialysis fluid to and used dialysis fluid from the dialyzer. Alternatively, the accuracy of the dialysis fluid pumps (e.g., membrane/volumetric) may be relied upon for controlling the volume of fresh and used fluid to and from the dialyzer, respectively. A separate ultrafiltration ("UF") pump may be used to remove a prescribed amount of UF from patient 12. Still further alternatively, fresh and used flowmeters may be used to control fresh and used dialysis fluid volume and UF. A dearation unit and dialysis fluid heater may be located upstream from the fresh dialysis fluid pump. The fresh dialysis fluid line may also be provided with one or more filter, such as an ultrafitler, to further purify the fresh dialysis fluid prior to delivery to the dialyzer. Dialysis fluid circuit 94 may be reused for multiple treatments, e.g., via heat and/or chemical disinfection, or be a single use disposable item. Dialysis fluid circuit 94 operates with multiple sensors such as pressure sensors, flow sensors, conductivity sensors, temperature sensors, blood leak detectors (e.g., optical sensors), and ammonia sensors. Dialysis fluid circuit 94 may further operate with a sorbent cartridge to regenerate used dialysis fluid.

Dialysis fluid for the HD version of machine 90 may be (i) bagged, (ii) regenerated via a sorbent device, or (iii) generated online using dry and/or liquid concentrates mixed with water purified and made suitable for HD ("WSHD"). WSHD is made via a water purifier or purification unit, which may be considered as part of machine 90 even if provided in a separate housing as the equipment performing HD. One suitable water purification unit is set forth in U.S. Patent Publication No. 2011/0197971, entitled, "Water Purification System and Method", filed Apr. 25, 2011, the entire contents of which are incorporated herein by reference and relied upon. In one embodiment, water purification unit includes filters and other structure to purify tap water (e.g., remove pathogens and ions such as chlorine), so that the water is in one implementation below 0.03 endotoxin units/ml ("EU/ml") and below 0.1 colony forming units/ml ("CFU/ml"). Again, the water purification unit may be provided in a housing separate from the housing of machine 90 performing HD.

Machine 90 may include a control unit 96 having one or more processor and memory that controls any of the electrically-controlled equipment and accepts electrical inputs from any electrically-outputting sensor provided in connection with the HD version of machine 90. Control unit 96 may for example include one or more primary control processor and memory that sends information to and receives data from one or more user interface processor and memory, which controls a user interface 98 of machine 90. User interface 98 may be provided with the chassis of machine 90 or be a tablet user interface. In the illustrated embodiment, control unit 96 accepts (wired or wirelessly) machine input data from, such as machine operating programs for patient 12, and sends machine and treatment operating data to, including patient data, a server such as server 60 and network 62, e.g., a cloud network. Server 60 and network 62 may incorporate the machine and treatment operating data, including patient data, for use with algorithms 64a to 64n and for incorporation into data sent back to patient devices 20, 40, 50 and/or to HCP devices 70, 80. Control unit 96 may also send and receive data, wired or wirelessly, to and from patient devices 20, 40, 50 directly.

Machine 90 is alternatively a peritoneal dialysis ("PD") machine. One suitable PD machine is set forth in U.S. Pat. No. 9,358,332, entitled, "Pump Cassette and Methods for Use in Medical Treatment System Using a Plurality of Fluid Lines", filed Dec. 9, 2010, the entire contents of which are incorporated herein by reference and relied upon. The PD version of medical fluid delivery machine 90 includes a disposable set 100 that mounts to the chassis of machine 90. Disposable set 100 includes a pumping cassette, which may be actuated pneumatically or via peristaltic pumping, and includes associated valving. Disposable set 100 may include pre-mixed PD solution or prepare solution on-line using one or more concentrate and purified water made suitable for PD ("WSPD"). Disposable set includes a patient line (single or dual lumen) leading from the pumping cassette to the patient. Disposable set 100 may further include a heater bag for heating PD dialysis fluid.

The chassis of the PD version of medical fluid delivery machine 90 includes a pump actuator (e.g., pneumatic or peristaltic), a heater, valve actuators (e.g., pneumatic or solenoid pinch valves), and sensors such as pressure sensors, temperature sensors, and conductivity sensors if needed. Control unit 96 operates with these devices as described above, including communication (wired or wirelessly) with server 60 and network 62 and/or patient devices 20, 40, 50.

Machine 90 is further alternatively an infusion pump, such as a large volume peristaltic or platen pump ("LVP") or a syringe pump. One suitable infusion pump is a Sigma® Pump marketed by the assignee of the present disclosure. Control unit 96 operates with the actuating and sensing devices of the infusion pump as described above, including communication (wired or wirelessly) with server 60 and network 62 and/or patient devices 20, 40, 50.

Figure 2:
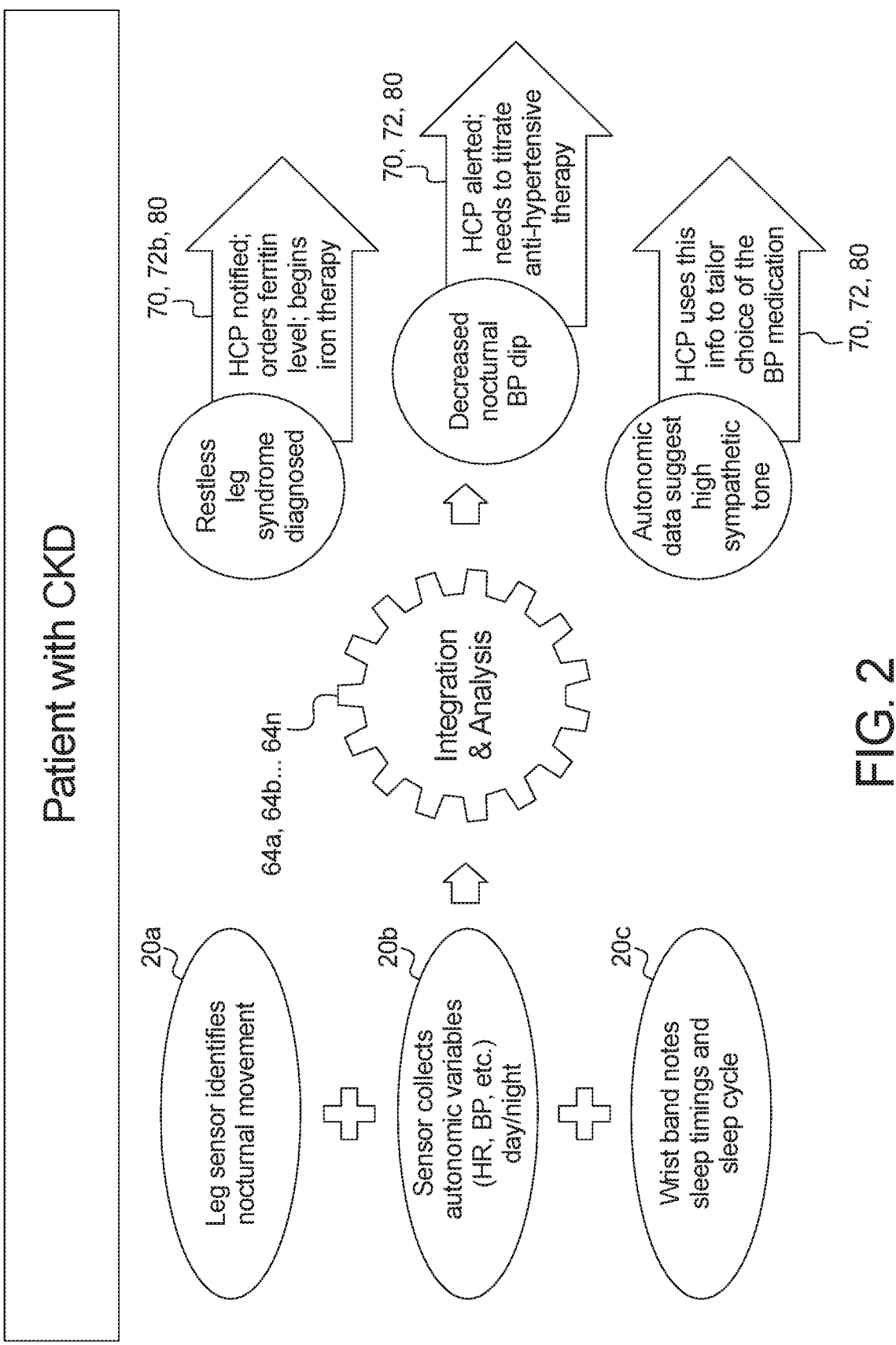
FIG. 2 is a schematic view illustrating example implementations of the present disclosure for a patient with chronic kidney disease.

Referring additionally to FIG. 2, in one example, existing chronic kidney disease ("CKD") patients are provided with at least one of a leg sensor 20a or a wristband sensor 20c. Leg sensor 20a may for example identify nocturnal leg movement. A second sensor 20b detects variables, such as heart rate and blood pressure. Wrist sensor 20c monitors the patient's sleep patterns, including sleep timings and sleep cycles. Data collected from sensors 20a, 20b and 20c is transmitted to software running algorithms 64a, 64b . . . 64n, which may for example compare the sensor data to one or more limit as described above. For example, nocturnal movement data from leg sensor 20a and/or sleep timings from sensor 20c may be compared to one or more limit or range (standard or specific to the patient) to determine if patient 12 has restless leg syndrome. If so, a health care provider ("HCP") may be notified automatically at an output device, e.g., smartphone 70, computer 72 and/or website 80, who may in response order a ferritin level blood test and possibly prescribe a treatment, such as an iron therapy.

In another example, blood pressure data from sensor 20b is monitored during the night to look at a nocturnal blood pressure dip for patient 12. If the blood pressure dip decreases, the HCP at smartphone 70, computer 72 and/or website 80 may be notified automatically to determine if an anti-hypertensive therapy for patient 12 should be titrated.

In a further example, blood pressure data from wrist sensor 20b is monitored to determine if autonomic data for patient 12 suggests high sympathetic tone. If so, the HCP at smartphone 70, computer 72 and/or website 80 may be notified automatically to perhaps modify the patient's blood pressure medicine.

Figure 3:
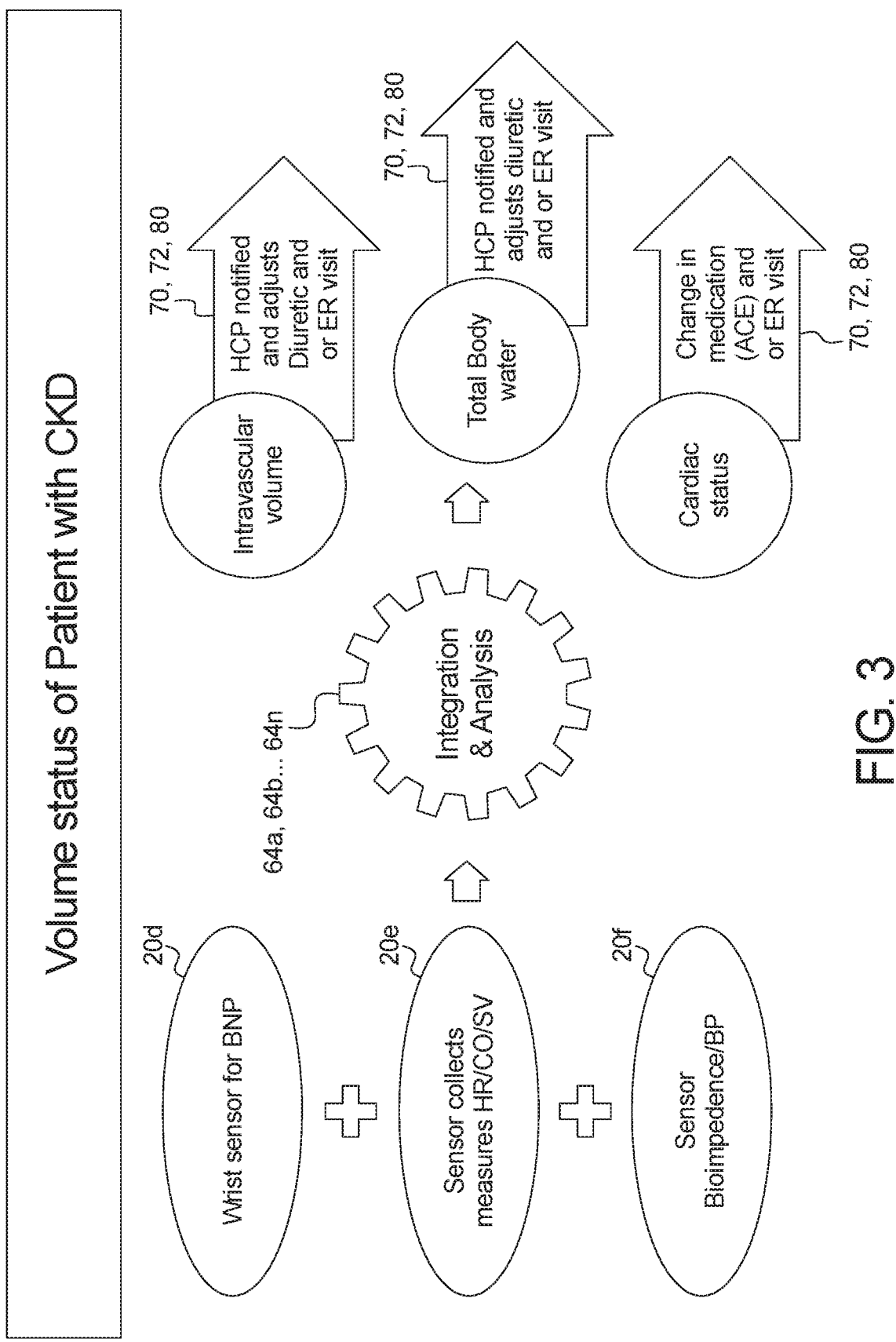
FIG. 3 is a schematic view illustrating example volume status implementations of the present disclosure for a patient with chronic kidney disease.

Referring additionally to FIG. 3, volume status examples concerning existing patients with end stage renal disease ("ESRD") include providing patient 12 with a wristband sensor 20d, for example, which measures B-type natriuretic peptide ("BNP"). Sensor 20e detects any one or more of heart rate ("HR"), cardiac output ("CO") and/or stroke volume ("SV"). Sensor 20f collects bioimpedance data and/or blood pressure. Data collected from sensors 20d to 20f is transmitted to software running algorithms 64a, 64b . . . 64n, which may for example compare the sensor data to one or more limit as described above. For example, the BNP or bioimpedance data may be compared to a limit or range to gauge the intravascular volume of patient 12, and if needed, a HCP at smartphone 70, computer 72 and/or website 80 may be notified automatically to adjust the patient's diuretic and/or schedule an emergency room visit. In another volume status example, BNP or bioimpedance data may be compared to a limit or range to gauge the total body water of patient 12, and if needed, a HCP at smartphone 70, computer 72 and/or website 80 may be notified automatically to again adjust the patient's diuretic and/or schedule an emergency room visit. In a further body status example, HR, CO and/or SV data may be compared to a limit or range, and if needed, a HCP at smartphone 70, computer 72 and/or website 80 may be notified automatically to evaluate the cardiac status of patient 12. If needed, the patient's angiotensin-converting enzyme ("ACE") medication may be changed and/or an emergency room visit may be scheduled.

Figure 4:
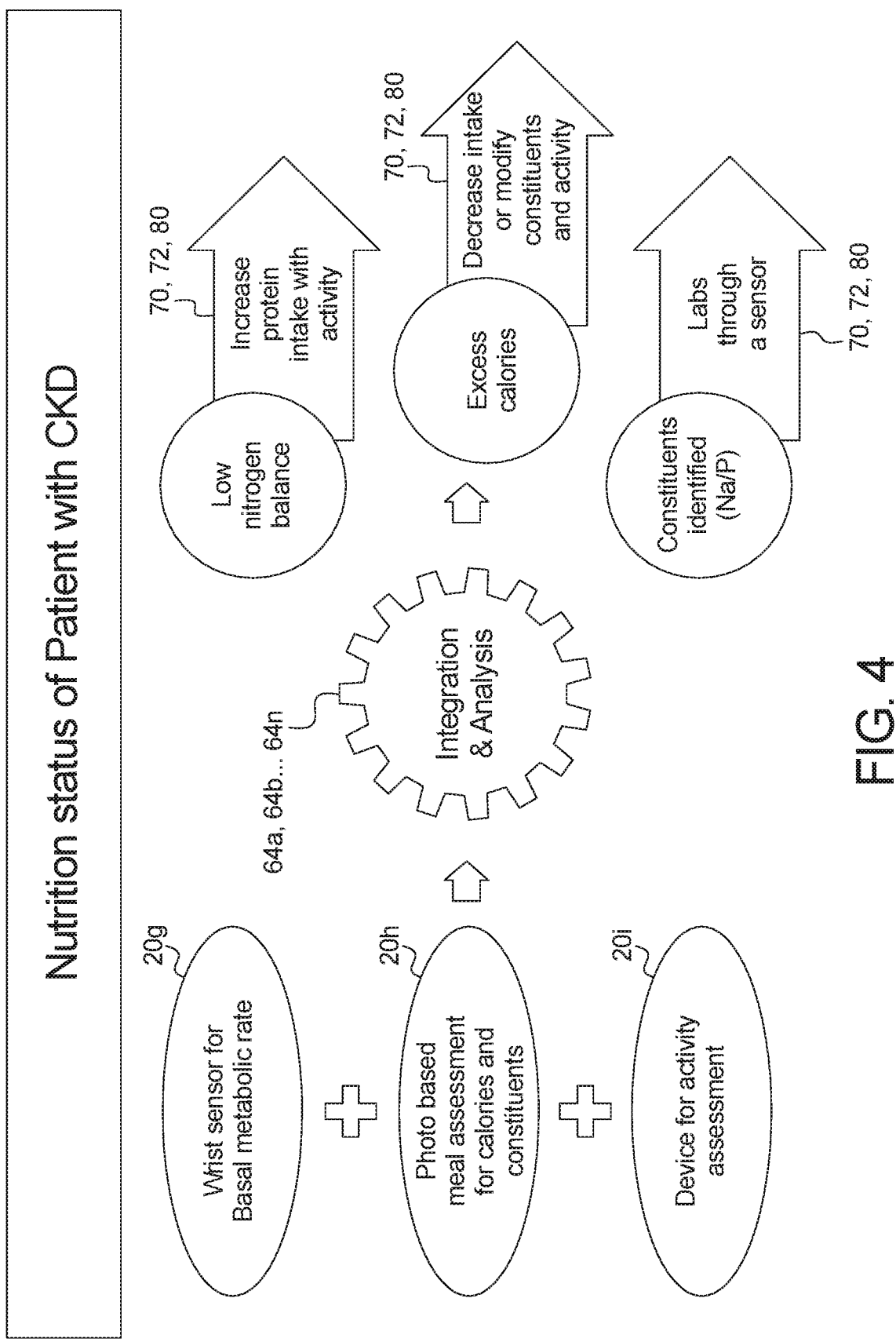
FIG. 4 is a schematic view illustrating example nutritional status implementations of the present disclosure for a patient with chronic kidney disease.

Referring additionally to FIG. 4, nutrition status examples concerning existing patients with ESRD include providing patient 12 with a wristband sensor 20g for measuring basal metabolic rate and/or assess the patient's physical activity. Alternatively or additionally, a camera 20h may be provided, which is used to take photographs of meals consumed by patient 12. The basal metabolic rate data may be compared to a limit or range at algorithm 64a, 64b . . . 64n to gauge the nutritional status of patient 12, such as whether patient 12 has a low nitrogen balance. If needed, an HCP at smartphone 70, computer 72 and/or website 80 may be notified automatically to prompt patient 12 to increase protein intake and/or physical activity. In another example, data from camera 20h may be analyzed at algorithm 64a, 64b . . . 64n to identify the foods and amounts consumed and to find caloric intake for each food and amount using a look-up table. Algorithm 64a, 64b . . . 64n then sums the caloric intake over a designated period, e.g., one day and compares the daily intake (may be averaged over multiple days) to a limit or range (standard or patient specific) to assess the patient's overall caloric intake. Data from sensor 20i may be used to assess the patient's activity level. If needed, an HCP at smartphone 70, computer 72 and/or website 80 may be notified automatically to prompt patient 12 to modify his or her diet to reduce calories. Data from camera 20h may be used alternatively or additionally to analyze the constituents of the patient's diet to identify constituents consumed, such as sodium (NA) and/or phosphorous (P).

FIGS. 1 to 4 illustrate that a given sensor 20 (referring to any of the sensors discussed herein, including sensors 20a to 20i) may sense one or multiple parameters. Also, multiple sensors 20 may be used on a single patient and multiple sensors 20 may be used for different patients. It is therefore contemplated for system 10 that in one embodiment, sensor 20 provides first sensed data and second, different sensed data, and wherein data analytics device 60 includes (i) a first algorithm 64a configured to analyze the first sensor data and provide a first analyzed data outcome to output devices 70, 72 and 80 and (ii) a second algorithm 64b configured to analyze the second sensor data and provide a second analyzed data outcome to output devices 70, 72 and 80.

In another embodiment for system 10, first sensor 20a to 20i provides first sensed data, and a second sensor 20a to 20i for a same patient 12 provides second, different sensed data, and wherein the data analytics device 60 includes (i) a first algorithm 64a that analyzes the first sensor data and provides a first analyzed data outcome to output devices 70, 72 and 80 and (ii) a second algorithm 64b that analyzes the second sensor data and provides a second analyzed data outcome to output devices 70, 72 and 80.

In a further embodiment for system 10, first sensor 20a to 20i provides a first sensed data type, and a second sensor 20a to 20i for a different patient 12 provides the same first sensed data type, and wherein data analytics device 60 includes a first algorithm 64a that analyzes the first sensor data type of both first and second sensors 20a and 20b and provides a first analyzed data outcome for the first sensor to output devices 70, 72 and 80 and a second analyzed data outcome for the second sensor to output devices 70, 72 and 80.

In still another embodiment for system 10, first sensor 20a to 20i provides a first sensed data, and second sensor 20a to 20i for a different patient 12 provides a second, different sensed data, and wherein the data analytics device 60 includes (i) a first algorithm 64a that analyzes the first sensor data and provides a first analyzed data outcome to output devices 70, 72 and 80 and (ii) a second algorithm 64b that analyzes the second sensor data and provides a second analyzed data outcome to output devices 70, 72 and 80.

The analyzed data outcome is in one embodiment useful in assessing a potential or current renal failure patient. At least one sensor 20 as alluded to above may contact the skin of patient 12 to non-invasively sense blood pressure, serum glucose, and/or nutritional parameters, which are then analyzed at data analytics device 60 using one or more algorithm 64a, 64b . . . 64n to provide the analyzed data feedback to patient 12 at patient devices 20, 40, 50 and/or to HCP at HCP devices 70, 80. To slow the progression of CKD, the analyzed data feedback may for example include a lifestyle modification, e.g., to reduce the body mass index ("BMI") of patient 12 to 20 to 25, to quit smoking, and/or to exercise more. Alternatively or additionally, to slow the progression of CKD, the analyzed data feedback may for example include nutritional interventions, e.g., to lower salt intake per day to at most 90 mmols or 2 grams. Alternatively or additionally, to slow the progression of CKD, the analyzed data feedback may provide patient 12 with medical management goals, including but not limited to: (i) reduce the blood pressure of patient 12 to at most 130/80 if an albuminuria ("Alb") to creatinine ratio ("ACR") for patient 12 is greater than 3 or to reduce the blood pressure of patient 12 to at most 140/90 if the Alb to creatinine ratio ("ACR") for patient 12 is less than or equal to 3, (ii) to reduce the blood glucose of patient 12 to alc being less than 7, and/or (iii) to reduce the albuminuria of patient 12 to ACR being less than 3.

To prevent complications associated with CKD, the analyzed data feedback from at least one sensor 20 may for example include anemia management, e.g., to maintain hemoglobin levels in patient 12 at less than 10 to 12 g/dL. Alternatively or additionally, to prevent complications associated with CKD, the analyzed data feedback from at least one sensor 20 may for example include bone disease management in which (i) phosphorous levels for patient 12 are maintained between 2.7 and 4.6 mg/dL, and/or (ii) a parathyroid ("PTH", calcium related) level for (a) a third stage CKD patient 12 is maintained between 35 to 70 pmol/L and for (b) a fourth stage CKD patient 12 is maintained between 70 to 110 pmol/L. Alternatively or additionally, to prevent complications associated with CKD, the analyzed data feedback from at least one sensor 20 may for example include cardiovascular disease management in which the blood pressure of patient 12 is managed along with other risk factors such as dyslipidemia. Alternatively or additionally, to prevent complications associated with CKD, the analyzed data feedback from at least one sensor 20 may for example include an assessment of the functional status or frailty of patient 12, and perhaps suggest exercise and/or rehab. Alternatively or additionally, to prevent complications associated with CKD, the analyzed data feedback from at least one sensor 20 may for example include a psychological assessment of the mental health of CKD patient 12, and perhaps suggest social work or psychological support.

Figure 5:
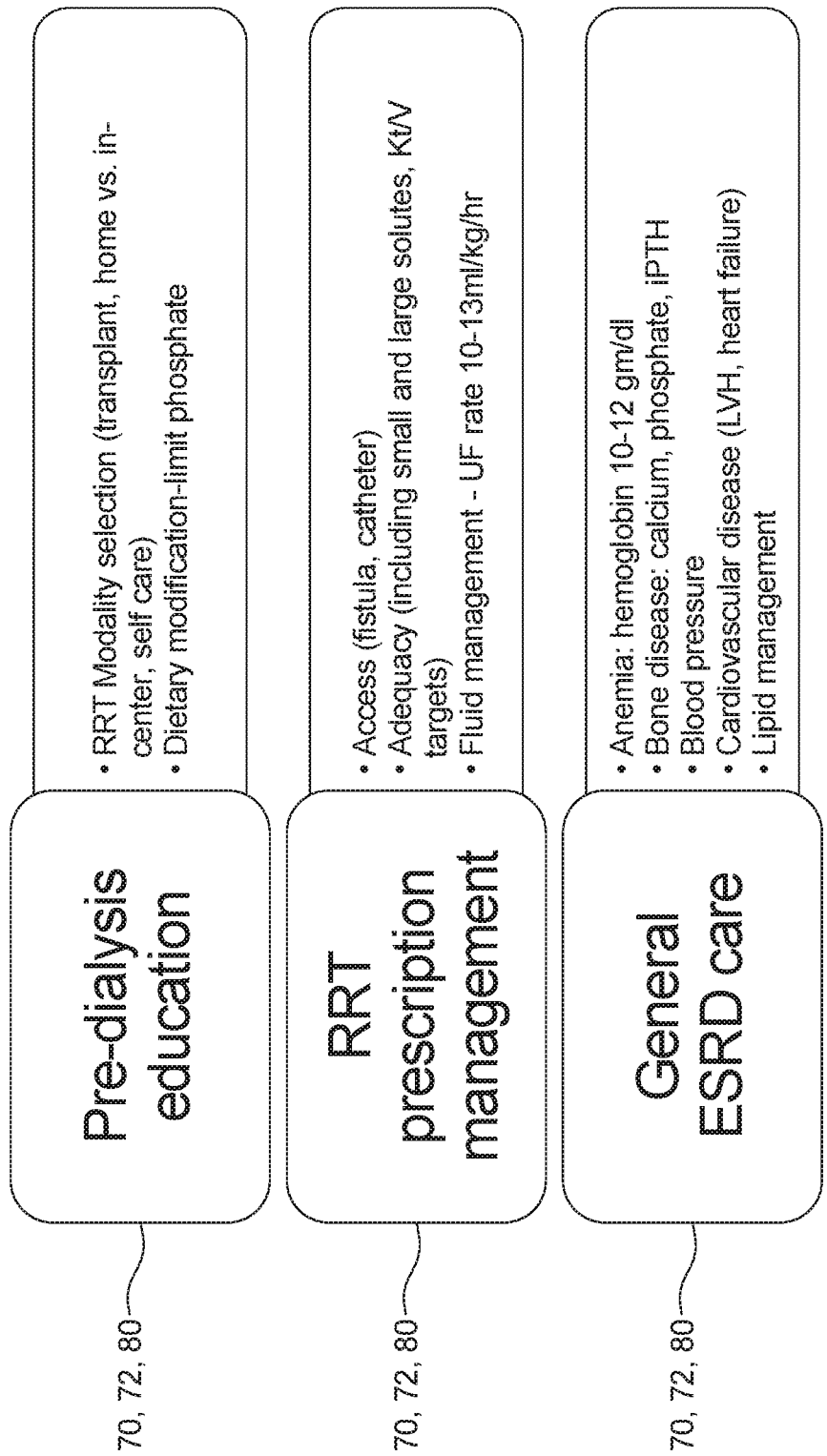
FIG. 5 is a schematic view illustrating different types of analyzed data outcomes of the present disclosure.

Referring now to FIG. 5, three types of analyzed data feedback or outputs from analytics device 60 using one or more algorithm 64a, 64b . . . 64n provided at output devices 70, 72 and 80 are illustrated schematically. Analyzed data output may include pre-dialysis education, including for example education regarding the types of renal replacement therapy ("RRT") and which to choose, e.g., kidney transplant, a home treatment, an in-center treatment or treatment at a self-care facility. Pre-dialysis education may also include dietary recommendations to delay the onset of CKD, e.g., to limit phosphate intake.

Analyzed data output may alternatively or additionally include RRT prescription management for current CKD patients 12. Here, information may be provided concerning how the CKD patient connects to a treatment machine or set, e.g., access information concerning fistulas and catheters for HD and patient transfer sets for PD. RRT prescription management information may alternatively or additionally be provided concerning treatment adequacy or how well the treatments are performing, which may be via a clearance determiner, such as Kt/V for both large and small molecules. RRT prescription management information may alternatively or additionally be provided concerning patient fluid management, e.g., is patient 12 removing the proper amount of UF and returning to his or her dry weight by the end of treatment.

Analyzed data output may alternatively or additionally include general ESRD care information or instructions, such as (i) for Anemia to limit hemoglobin to 10 to 12 gm/dl, (ii) for bone disease to limit calcium, phosphate and intact parathyroid hormone ("iPTH") levels, (iii) to keep blood pressure below a desired level, (iv) cardiovascular disease care information and/or (v) lipid management information.

Figure 6:
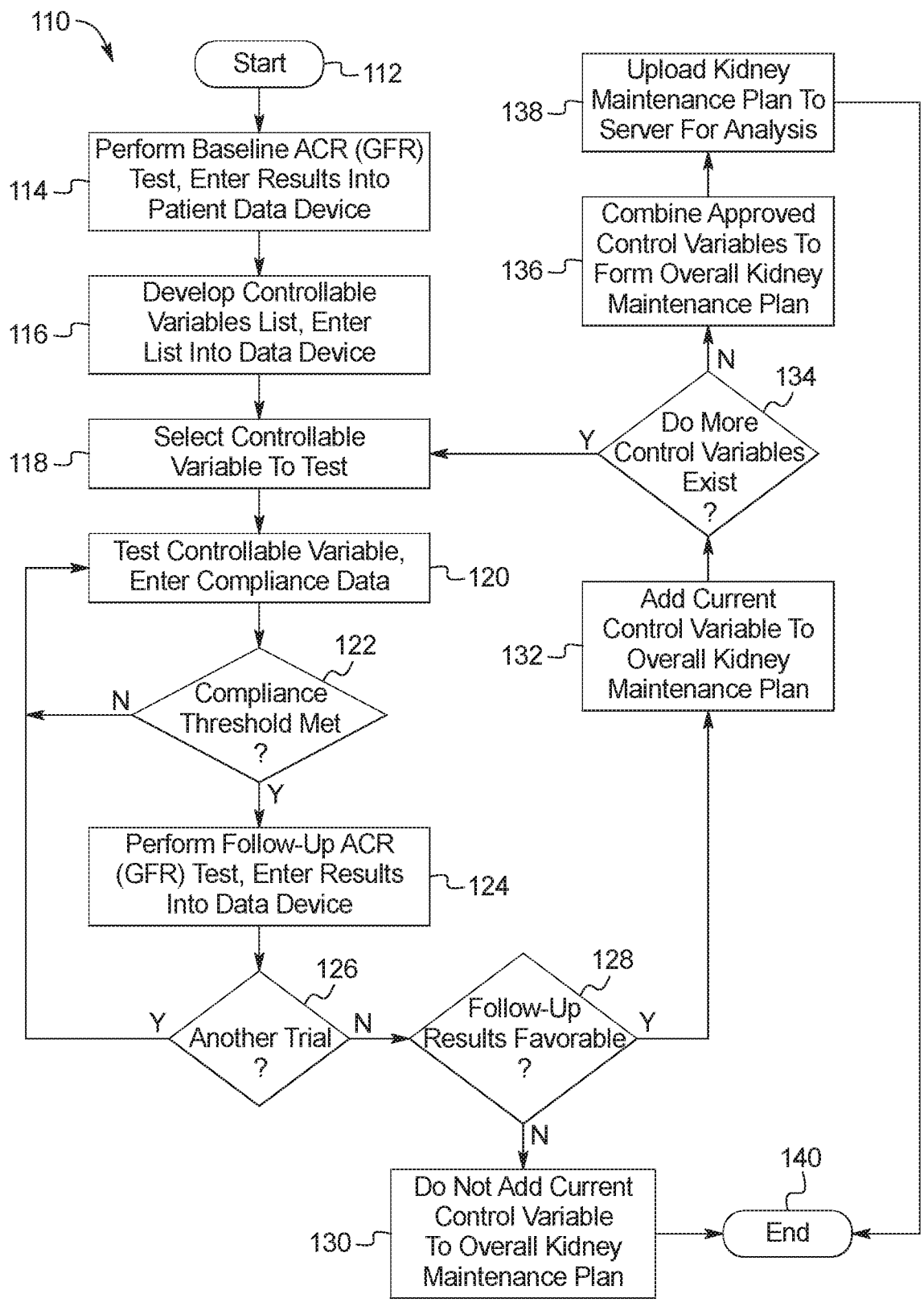
FIG. 6 is a process flow diagram illustrating one embodiment of a learning method for preventing, delaying or stemming kidney failure and/or kidney function loss, and which may be implemented using the system of FIG. 1.

Referring now to FIG. 6, one embodiment for an intelligent learning method operable with system 10 described above is illustrated by method 110. Method 110 is geared towards helping people who show at risk factors for kidney disease or who are in the beginning stages of kidney disease. The well accepted test for accessing a person's kidney function is a glomerular filtration rate ("GFR") test. GFR is estimated from a simple blood test. Tracking a person's GFR allows one to see if a person's kidney function is staying the same or getting worse. With GFR, the higher number the better: (i) GFR at 90 or above with no kidney damage or better means the patient has full functioning kidneys but may still have at risk factors, such as, diabetes, high blood pressure, family history, older age, or ethnic groups; (ii) Stage 1—kidney damage exists, e.g., Albumin detected, with normal kidney function at 90 or above; (iii) Stage 2—kidney damage detected with mild loss of kidney function, GFR at 89 to 60; (iv) Stage 3a—mild to moderate loss of kidney function, GFR at 59 to 44, (v) Stage 3b—moderate to severe loss of kidney function, GFR at 44 to 30, (vi) Stage 4—severe loss of kidney function, GFR at 29 to 15, Stage 5—kidney failure, GFR at less than 15.

Thus the primary goals of method 110 are to keep group (i) people from entering the Stages and groups (ii) to (v) people from getting worse. Even people with kidney failure have some remaining kidney function. As mentioned above, kidney failure is not the same as loss of kidney function. Kidney failure may be detected by looking for a protein called Albumin, which is made from food that is consumed. Albumin circulates in a person's blood and is used by the person's body. Healthy kidneys do not excrete albumin. Having albumin in the urine is called "albuminuria" and is a sign of kidney damage. Having albumin in the urine for three consecutive months according to the National Kidney Foundation means that the patient has chronic kidney disease. A simple urine test is performed to look for a albumin-to-creatinine ratio ("ACR") as discussed above. In an embodiment, method 110 uses the ACR (and/or GFR) test as feedback for its learning.

In an embodiment, method 110 is a patient-implemented, caregiver assisted method, which is carried out primarily at the patient's smartphone 40 or computer 50 in combination with one or more sensor 20. At oval 112, method 110 begins. At block 114, patient 12 performs an initial ACR (and/or GFR) test and enters an initial ACR result into the patient's smartphone 40 or computer 50. At block 116 (which may be performed before or after block 114) patient 12, e.g., in cooperation with a doctor or clinician, develops a list of controllable variables selected to determine their effect, if any, on albumin output in the patient's urine. The list is entered into smartphone 40 or computer 50.

Controllable variables that may be entered at block 116 include, for example, dietary restrictions, such as, (i) reduce phosphorous in the patient's diet, (ii) reduce calcium in the patient's diet, (iii) reduce sodium in the patient's diet, (iv) reduce or eliminate alcohol, (v) drink a prescribed amount of water every day, (vi) drink a prescribed amount of green tea or other antioxidant every day, (vii) reduce sugar intake every day, and (vii) take a prescribed amount of a particular vitamin every day. Controllable variables at block 116 may also include lifestyle adjustments, such as, (i) be in bed by a certain hour every day, (ii) perform a certain amount of exercise per week, or (iii) eliminate food consumption after a certain time each day. Controllable variables at block 116 may further include medicinal adjustments, such as (i) taking a blood pressure reducing drug, or (ii) taking an appetite suppressing drug.

Sensors 20 that may be used with the list of controllable variables include but are not limited to (a) a blood pressure sensor, (b) a weight scale, (c) a heart rate or sleep pattern sensor, or (d) a camera to show compliance, e.g., for dietary intake.

Once the list of variables is entered into the patient's smartphone 40 or computer 50 at block 116, method 110 at smartphone 40 or computer 50 selects, or the patient selects, a first or a next one of the controllable variables to analyze as illustrated at block 118. At block 120, the patient performs the selected control variable modification over a suitable time period, e.g., twenty days or a month, and enters compliance confirmation into a compliance entry screen displayed at smartphone 40 or computer 50 at a desired interval, e.g., daily. For example, once every day, patient 12 may confirm at smartphone 40 or computer 50 that the patient has consumed less than a maximum amount of phosphorous, calcium, sodium, alcohol or sugar. Or for example, once every day, patient 12 may confirm at smartphone 40 or computer 50 that the patient has consumed a minimum amount of pure water, green tea or other antioxidant, or specified vitamin. Or for example, once every day, patient 12 may confirm at smartphone 40 or computer 50 that the patient has gone to bed gone to bed the night before by a certain hour, has performed a certain amount of exercise that may be accumulated on a per week basis, or has eliminated food consumption after a certain time. Or for example, once every day, patient 12 may confirm at smartphone 40 or computer 50 that the patient has taken a prescribed amount of a blood pressure reducing drug, or taken an appetite suppressing drug.

Sensors 20 may be used for compliance verification or to accompany and verify the patient's compliance entries. For example, the heart rate monitor may be used to check consistency with (i) the patient's entry that the patient went to bed at a prescribed time or (ii) the patient's entry that the patient exercised on a particular day. Software at smartphone 40 or computer 50 may also accept or require that the patient submit one or more timestamped photograph of the patient's food for the day, e.g., food as prepared or food label, to verify compliance with a controllable nutritional variable. Software at smartphone 40 or computer 50 may also accept outputs from a blood pressure monitor to verify that the patient is taking prescribed blood pressure medicine and that the medicine is working properly.

At diamond 122, when the control variable modification has been performed over the set time period, software at smartphone 40 or computer 50 in one embodiment determines whether a compliance threshold has been met. The compliance threshold may be different for different control variables. For example, a nutritional control variable may be set for 80% compliance, a lifestyle control variable may be set for 70% compliance, while a medicinal control variable may be set for 90% compliance. Compliance percentages may be preset into the software at smartphone 40 or computer 50 or be set by the doctor or clinician prior to commencing method 110. If the compliance threshold has not been met as determined at diamond 122, method 110 returns to block 120 for the same control variable. The loop between block 120 and diamond 122 is repeated until the compliance threshold for the same control variable has been met.

If the compliance threshold for the current control variable has been met as determined at diamond 122, method 110 at block 124 prompts patient 12 to perform a follow-up ACR (and/or GFR) test and to enter a follow-up ACR result into the patient's smartphone 40 or computer 50. It should be appreciated that the GFR tests may be performed alternatively or in addition to the ACR tests at blocks 114 and 124.

At diamond 126, regardless of the follow-up ACR (GFR) result in one embodiment, method 110 determines whether another trial for the same control variable should be performed. Certain control variables may only warrant a single trial, while other control variables may warrant two or more trials for repeatability. Whether or not an additional trial for a particular control variable is performed may be preset into the software at smartphone 40 or computer 50 or be set by the doctor or clinician prior to commencing method 110.

If another trial for the current control variable exists as determined at diamond 126, then method 110 returns to block 120 for the same control variable. The loop between block 120 and diamond 126 is repeated until there is no other trial for the current control variable as determined at diamond 126.

When there is no additional trial as determined at diamond 126, method 110 at diamond 128 determines whether the follow-up ACR result, or the combined follow-up results from multiple trials, indicate(s) that the patient's kidney failure is worsening. If so, as determined at diamond 128, then the current control variable for patient 12 at block 130 is determined not to be part of the patient's overall kidney maintenance plan. There may be other reasons for patient 12 to manage the current control variable but not for the patient's overall kidney maintenance plan. If the follow-up ACR result, or the combined follow-up results from multiple trials, instead indicate(s) that the patient's kidney failure is not worsening or is improving, as determined at diamond 128, then the current control variable for patient 12 at block 132 is determined to be part of the patient's overall kidney maintenance plan. That is, the doctor or clinician will urge patient 12 to continue to manage the particular control variable in the manner set forth at block 120.

Combining results from multiple trials may be done by a straight average, e.g., add the two ACR results and divide by two, or be weighted based upon compliance, e.g., a 70% compliance result is allowed seven entries, while a 90% compliance result is allowed nine entries, which are all added together and divided by sixteen.

At diamond 134, method 110 determines whether another control variable is set for analysis at block 116. If another control variable exists at block 116, as determined at diamond 134, then method 110 returns to block 118, where another control variable is selected, and the loop between block 118 and diamond 134 is repeated until there is no additional control variable to analyze, as determined at diamond 134.

At diamond 134, when there is no additional control variable to analyze, method 110 at block 136 combines all control variables from block 132 determined to be part of the patient's overall kidney maintenance plan to form the plan. Smartphone 40 or computer 50 thereafter implements, monitors and controls the overall kidney maintenance plan. For each control variable of the overall kidney maintenance plan, smartphone 40 or computer 50 prompts patient 12 to enter compliance information and/or receives compliance information or data from one or more sensor 20.

At block 138, smartphone 40 or computer 50 uploads the overall kidney maintenance plan for patient 12 to server 60 and network 62 and/or to HCP devices 70, 72. The upload may be with patient 12 identification data, may be stripped completely of such data, or may be provided with generalized patient data, e.g., age, sex, existing kidney disease and function levels, etc. One or more algorithm 64*a* to 64*n* is programmed to combine multiple overall kidney maintenance plans to look for trends and identify which control variables, and possibly which combinations of control variables, appear to be most effective and therefore preferred. The results may be generalized for all patients 12 and/or be categorized for different subsets of patients 12, e.g., age, sex, existing kidney disease and function levels. The results may be used to develop more effective and/or streamlined lists of control variables entered at block 116.

At oval 140, method 110 ends.

Method 110 performed at system 10 is accordingly a learning method on multiple levels. A first level is a subjective patient level, in which control variables for a given patient 12 are optimized, and wherein different control variables for different patients are able to be managed. The second learning level is a macroscopic level, which finds trends in the control variables that apply to all patients 12 or to a particular subset of patients 12. Method 110 is also a learning method from the standpoint that new control variables may be added to an overall pool of control variables as the new control variables come to light.

Figure 7:
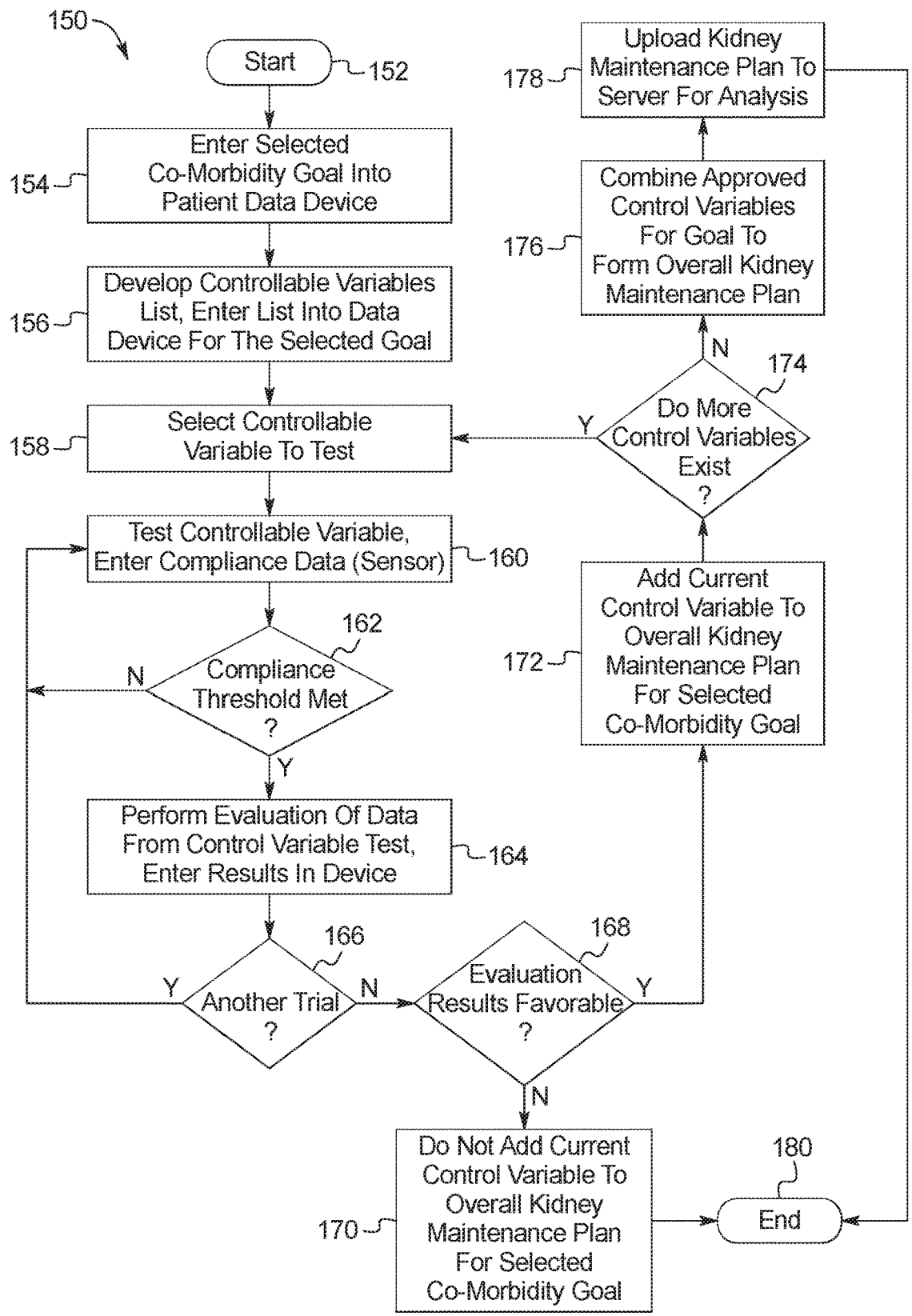
FIG. 7 is a process flow diagram illustrating one embodiment of a learning method for preventing, delaying or stemming co-morbidity factors for patients undergoing treatment via a dialysis machine, and which may be implemented using the system of FIG. 1.

Method 110 may be performed while patient 12 is or is not being treated by medical fluid delivery machine 90. Medical fluid delivery machine 90 is nevertheless not required to perform method 110. Referring now to FIG. 7, method 150 performed at system 10 illustrates a method that incorporates treatments via medical fluid delivery machine 90. The goal of method 150 is in one embodiment to minimize a particular co-morbidity factor, such as patient volume (leading to heart disease), blood pressure (leading to heart disease or stroke), or blood sugar (leading to diabetes).

In an embodiment, method 150 is a patient-implemented, caregiver assisted method, which is again carried out primarily at the patient's smartphone 40 or computer 50 in combination with one or more sensor 20. At oval 152, method 150 begins. At block 154, patient 12 enters into the patient's smartphone 40 or computer 50 a co-morbidity goal, such as to (i) regulate patient volume, (ii) regulate blood pressure, or (iii) regulate blood sugar.

At block 156 (which may be performed before or after block 154) patient 12, e.g., in cooperation with a doctor or clinician, develops a list of controllable variables selected to determine their effect, if any, on the selected goal entered at block 154. For example, controllable variables for patient volume include (i) limit the weight of food consumed per day to a certain amount, (ii) limit the weight of liquid consumed per day to a certain amount, (iii) limit the weight of food and liquid consumed per day to a certain amount, (iv) regulate the amount of food and/or liquid consumed after treatment, so that a greater percentage of food and/or liquid is consumed, e.g., closer to (or farther from) the next dialysis treatment, or if dialysis treatment is daily to ingest food on a daily basis closer to (or farther from) the next treatment.

Controllable variables for patient blood pressure include (i) limit sodium intake, (ii) limit sodium level of dialysis fluid used during treatment, (iii) limit fatty foods, and (iv)

limit alcohol intake. Controllable variables for patient blood sugar include (i) limiting sugar intake and (ii) limiting dextrose or glucose levels in peritoneal dialysis fluids.

Method 150 in one embodiment uses sensors 20 for both evaluation and compliance purposes. Example sensors 20 used for patient volume include weigh scales both to weigh patient 12 (for evaluation) and the food and/or water consumed by the patient (for compliance). Example sensors 20 used for patient blood pressure include blood pressure monitors (for evaluation) and cameras (for compliance) used for reading sodium levels on labels. Example sensor(s) 20 used for patient blood sugar include glucose meters (for evaluation) and cameras (for compliance) used for reading dextrose and glucose levels on labels.

Once the list of controllable variables for the selected co-morbidity goal is entered into the patient's smartphone 40 or computer 50 at block 156, method 150 at smartphone 40 or computer 50 selects, or the patient selects, a first or a next one of the controllable variables to analyze as illustrated at block 158. At block 160, patient 12 performs the selected control variable modification over a suitable time period, e.g., twenty days or a month, and if applicable enters compliance confirmation into a compliance entry screen displayed at smartphone 40 or computer 50 at a desired interval, e.g., daily. For patient volume for example, once every day, patient 12 may confirm at smartphone 40 or computer 50 that the patient has consumed less than a weight limit of food and/or liquid. Patient 12 may for example be required to weigh all food or liquid, which is sent from sensor 20 to smartphone 40 or computer 50. For patient blood pressure, patient 12 may confirm at smartphone 40 or computer 50 that the patient has consumed less than a prescribed limit of sodium. Patient 12 may for example be required to photograph all food and/or liquids for sodium levels, which are sent from sensor 20 to smartphone 40 or computer 50. For patient blood sugar, patient 12 may confirm at smartphone 40 or computer 50 that the patient has consumed less than a prescribed limit of dextrose or glucose. Patient 12 may for example be required to photograph all food and/or liquids for dextrose or glucose levels, which are sent from sensor 20 to smartphone 40 or computer 50.

At block 160, during testing for the control variable, sensors 20 used for evaluation send evaluation data to smartphone 40 or computer 50, which data may in turn be sent to server 60 and network 62 for dissemination to website 80 at HCP's smartphone 70 or computer 72. For the goal of patient volume, patient weight data via a weigh scale is delivered on a periodic basis, including patient weight before and after each dialysis treatment. For the goal of patient blood pressure, patient blood pressure data via a blood pressure monitor is delivered on a periodic basis, including patient blood pressure before and after each dialysis treatment. For the goal of patient blood sugar, patient blood sugar data via a glucose monitor is delivered on a periodic basis, including patient blood sugar before and after each dialysis treatment.

At diamond 162, when the control variable modification has been performed over the set time period, software at smartphone 40 or computer 50 in one embodiment determines whether a compliance threshold has been met. The compliance threshold may be different for different control variables and different co-morbidity goals. For example, a nutritional control variable may be set for 80% compliance, while a treatment control variable (e.g., sodium or dextrose levels in dialysis fluids) may be set for 95% compliance. Compliance percentages may be preset into the software at smartphone 40 or computer 50 or be set by the doctor or clinician prior to commencing method 150. If the compliance threshold has not been met as determined at diamond 162, method 150 returns to block 160 for the same control variable. The loop between block 160 and diamond 162 is repeated until the compliance threshold for the same control variable has been met.

If the compliance threshold for the current control variable has been met as determined at diamond 162, method 150 at block 164 evaluates the evaluation data sent from evaluation sensors 20. The evaluation may be performed at smartphone 40 or computer 50, on an algorithm 64a to 64n at server 60 and network 62 or perhaps at website 80. The evaluation in one embodiment determines a deviation from a desired or expected value. For patient volume, for example, one goal of dialysis treatment is to return patient 12 to his or her dry weight, which is the weight of the patient assuming the patient has normally functioning kidneys. It is also the weight that patient 12 is supposed to have at the end of a dialysis treatment. Dry weight is typically determined by the patient's doctor or clinician and is thus known to method 150 and system 10. Thus one deviation evaluation is determining how far the patient's actual weight is from the patient's dry weight just before treatment. The less the better, resulting in less UF to remove over treatment. Reducing the amount of UF to remove helps during HD because patient 12 is less prone to feeling dizzy. Reducing the amount of UF to remove helps during PD because patient 12 may use a lower dextrose level dialysis fluid, which is beneficial from a blood sugar perspective. Moreover, reducing patient volume in general reduces stress placed on the patient's heart.

For patient blood pressure, for example, the deviation evaluation may look for how far off the patient's blood pressure is on average over the evaluation period (including during treatments) from a desired blood pressure for patient 12. For patient blood sugar, for example, the deviation evaluation may look for how far off the patient's blood sugar is on average over the evaluation period (including during treatments) from a desired blood sugar. Method 150 in an embodiment sets an allowable deviation amount from the desired amounts. Falling within the deviation amount yields a favorable result according to one embodiment of method 150. Falling outside the deviation amount yields a non-favorable result according to one embodiment of method 150.

At diamond 166, regardless of the deviation evaluation result in one embodiment, method 150 determines whether another trial for the same control variable should be performed. Certain control variables may only warrant a single trial, while other control variables may warrant two or more trials for repeatability. Whether or not an additional trial for a particular control variable is performed may be preset into the software at smartphone 40 or computer 50 or be set by the doctor or clinician prior to commencing method 150.

If another trial for the current control variable exists as determined at diamond 166, then method 150 returns to block 160 for the same control variable. The loop between block 160 and diamond 166 is repeated until there is no other trial for the current control variable as determined at diamond 166.

When there is no additional trial as determined at diamond 166, method 150 at diamond 168 determines whether the deviation evaluation result, or the combined deviation evaluation results from multiple trials, indicate(s) that the particular co-morbidity goal is being aided or assisted. If not, as determined at diamond 168, then the current control variable for the current co-morbidity goal for patient 12 at block 170 is determined not to be part of the patient's overall kidney treatment plan. There may be other reasons for patient 12 to manage the current control variable but not for the patient's overall kidney maintenance plan. If the deviation evaluation result, or the combined deviation evaluation results from multiple trials, instead indicate(s) that the co-morbidity goal is being aided or assisted via the modification of the controllable variable, as determined at diamond 168, then the current control variable for patient 12 at block 172 is determined to be part of the patient's overall kidney maintenance plan for the particular co-morbidity goal. That is, the doctor or clinician will urge patient 12 to continue to manage the particular control variable in the manner set forth at block 160.

Combining results from multiple trials may be done by a straight average, e.g., add the deviation evaluation results and divide by two, or be weighted based upon compliance, e.g., a 80% compliance result is allowed eight entries, while a 90% compliance result is allowed nine entries, which are all added together and divided by seventeen.

At diamond 174, method 150 determines whether another control variable is set for analysis at block 156. If another control variable exists at block 156, as determined at diamond 174, then method 150 returns to block 158, where another control variable is selected, and the loop between block 158 and diamond 174 is repeated until there is no additional control variable to analyze, as determined at diamond 174.

At diamond 174, when there is no additional control variable to analyze, method 150 at block 176 combines all control variables from block 172 determined to be part of the patient's overall kidney maintenance plan, for the particular co-morbidity goal, to form the plan. Smartphone 40 or computer 50 thereafter implements, monitors and controls the overall kidney maintenance plan. For each control variable of the overall kidney maintenance plan, smartphone 40 or computer 50 prompts patient 12 to enter compliance information and/or receives compliance information or data from one or more sensor 20.

At block 178, smartphone 40 or computer 50 uploads the overall kidney maintenance plan for patient 12 to server 60 and network 62 and/or to HCP devices 70, 72, e.g., for display at website 80. The upload may be with patient 12 identification data, may be stripped completely of such data, or may be provided with generalized patient data, e.g., age, sex, existing kidney disease and function levels, etc. One or more algorithm 64a to 64n is programmed to combine multiple overall kidney maintenance plans (for the particular co-morbidity goal) to look for trends and identify which control variables, and possibly which combinations of control variables, appear to be most effective and therefore preferred. The results may be generalized for all patients 12 and/or be categorized for different subsets of patients 12, e.g., age, sex, existing kidney disease and function levels. The results may be used to develop more effective and/or streamlined lists of control variables entered at block 156.

At oval 180, method 150 ends. Method 150 may then be repeated at system 10 for another co-morbidity goal, such as any of the remaining ones of (i) regulating patient volume, (ii) regulating blood pressure, or (iii) regulating blood sugar.

Methods 110 and 150 have been described above using the patient's smartphone 40 or computer 50 as the evaluating devices as the decision maker and the evaluator up until the kidney maintenance plan uploading steps 138 (method 110) and 178 (method 150). It should be appreciated that any of the following method steps may be performed alternatively or additionally at any one or more of server 60, e.g., via one or more algorithm 64a to 64n, HCP smartphone 70 or HCP computer 72, e.g., in connection with website 80 for method 110: (i) baseline ACR (GFR) results at block 114 may be stored remotely, (ii) developing and storing controllable variables list at block 116 may be performed remotely, (iii) selecting a controllable variable to test at block 118 may be performed remotely, (iv) results from testing the controllable variables at block 120 may be stored remotely, entering compliance data if done by patient is done at smartphone 40 or computer 50 but data could be stored remotely, entering compliance data if provided via a sensor 20 could be sent remotely, bypassing smartphone 40 or computer 50 or using smartphone 40 or computer 50, (v) compliance threshold determination at diamond 122 may be performed remotely, (vi) results from follow-up ACR (GFR) at block 124 may be stored remotely, (vii) determining whether another trial exists at diamond 126 may be performed remotely, (viii) determining whether follow-up ACR (GFR) results are favorable at diamond 128 may be performed remotely, (ix) adding current control variable to an overall kidney maintenance plan at block 132 may be performed remotely, (x) determining whether more variables exist at diamond 134 may be done remotely, and (xi) forming the overall maintenance plan at block 136 may be performed remotely.

Any of the following method steps may be performed alternatively or additionally at any one or more of server 60, e.g., via one or more algorithm 64a to 64n, HCP smartphone 70 or HCP computer 72, e.g., in connection with website 80 for method 150: (i) entering the co-morbidity goal at block 154 may be performed and stored remotely, (ii) developing and storing controllable variables list at block 156 may be performed remotely, (iii) selecting a controllable variable to test at block 158 may be performed remotely, (iv) results from testing controllable variables at block 160 may be done remotely, entering compliance data if done by patient is done at smartphone 40 or computer 50 but data could be stored remotely, entering compliance data if provided via a sensor 20 could be sent remotely, bypassing smartphone 40 or computer 50 or using smartphone 40 or computer 50, (v) compliance threshold determination at diamond 162 may be performed remotely, (vi) performing evaluation of data from control variable test at 164 may be stored remotely, (vii) determining whether another trial exists at diamond 166 may be performed remotely, (viii) determining whether the evaluation results are favorable at diamond 168 may be performed remotely, (ix) adding current control variable to an overall kidney maintenance plan at block 172 may be performed remotely, (x) determining whether more variables exist at diamond 174 may be done remotely, (xi) forming the overall maintenance plan at block 176 may be performed remotely.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A personalized renal failure chronic care system for a patient comprising:
    a patient data input and output device;
    a sensor communicatively coupled to the patient data input and output device and configured to record, as compliance information, at least one of blood pressure data, glucose data, bioimpedance data, heart rate data, movement data, or nutritional data from the patient;

a server operating over a network, the server communicatively coupled to the sensor via a connection to the patient data input and output device over the network;

a health care provider ("HCP") data input and output device in communication with the server via the network;

software stored on the server or the HCP data input and output device, the software including an automated learning method for creating an overall kidney maintenance plan that specifies one or more controllable variables as actions performed by the patient to prevent or reduce complications associated with chronic kidney disease ("CKD"), the automated learning method configured to present a plurality of controllable variables for selection, wherein the controllable variables for selection include at least one nutritional variable related to a dietary adjustment and at least one lifestyle variable related to a lifestyle adjustment, and wherein a selected controllable variable is scheduled to be modified for the patient over a testing period; and a compliance entry feature configured to receive the compliance information from the sensor, wherein the automated learning method is configured to use the compliance information to confirm that the selected controllable variable was modified over the testing period as scheduled, wherein the automated learning method is configured to perform an evaluation to determine whether the selected controllable variable is to be included in the overall kidney maintenance plan, the evaluation including receiving first evaluation data as a baseline, the first evaluation data related to a chronic kidney disease test of the patient performed during a first time of the testing period, receiving second evaluation data that is related to the chronic kidney disease test of the patient performed during a subsequent, second time of the testing period, determining from the first evaluation data and the second evaluation data whether a kidney function worsens, adding the selected controllable variable to the overall kidney maintenance plan as an approved controllable variable when (i) a worsening of kidney function is not determined between the first evaluation data and the second evaluation data, and (ii) the compliance information provides a confirmation that the selected controllable variable was modified over the testing period, and omitting the selected controllable variable from the overall kidney maintenance plan when a worsening is determined between the first evaluation data and the second evaluation data, wherein the software is configured to transmit the overall kidney maintenance plan including at least one approved controllable variable over the network to the patient data input and output device to implement or control adherence to the overall kidney maintenance plan.

2. The personalized renal failure chronic care system of claim 1, wherein the inclusion of the approved controllable variable in the overall kidney maintenance plan is performed to slow or stop the spread of kidney disease or loss of kidney function, and wherein the chronic kidney disease test includes at least one of an albumin-to-creatinine ratio ("ACR") test or a glomerular filtration rate ("GFR") test performed on the patient.

3. The personalized renal failure chronic care system of claim 2, wherein the evaluation results in the selected controllable variable being included in the overall kidney maintenance plan if the at least one ACR or GFR test does not show worsening of kidney disease or loss of kidney function.

4. The personalized renal failure chronic care system of claim 1, wherein the nutritional variable is related to a dietary restriction and the lifestyle variable is related to a lifestyle adjustment.

5. The personalized renal failure chronic care system of claim 1, wherein the nutritional variable includes at least one of (i) phosphorous to be reduced in the patient's diet, (ii) calcium to be reduced in the patient's diet, (iii) sodium to be reduced in the patient's diet, (iv) alcohol consumption to be reduced, (v) water to be consumed in a prescribed amount, (vi) an antioxidant to be consumed in a prescribed amount, (vii) sugar consumption to be reduced, or (viii) a vitamin consumed in a prescribed amount.

6. The personalized renal failure chronic care system of claim 1, wherein the lifestyle variable includes at least one of (i) going to sleep by a prescribed hour in a day, (ii) performing a certain amount of exercise, or (iii) eliminating food consumption after a certain time in a day.

7. The personalized renal failure chronic care system of claim 1, wherein the controllable variables additionally include a medicinal variable comprising at least one of a blood pressure reducing drug or an appetite suppressing drug.

8. The personalized renal failure chronic care system of claim 1, which includes a second sensor having an output used for or in combination with the compliance information that the controllable variable is modified over the testing period as scheduled.

9. The personalized renal failure chronic care system of claim 1, wherein the sensor includes (i) a heart rate monitor, (ii) a camera producing a timestamped photograph of the patient's food, or (iii) a blood pressure monitor.

10. The personalized renal failure chronic care system of claim 1, wherein the inclusion of the approved controllable variable in the overall kidney maintenance plan is performed to slow or stop a co-morbidity factor affected by the controllable variable, and wherein the evaluation includes determining an effect of the controllable variable on the co-morbidity factor relative to a desired value for the co-morbidity factor.

11. The personalized renal failure chronic care system of claim 10, wherein a first co-morbidity factor is patient volume leading to heart failure, a second co-morbidity factor is patient blood pressure leading to heart failure or stroke, and a third co-morbidity factor is patient blood sugar leading to diabetes.

12. The personalized renal failure chronic care system of claim 10, wherein the plurality of controllable variables for selection are associated with a co-morbidity factor selected from a plurality of co-morbidity factors.

13. The personalized renal failure chronic care system of claim 12, wherein the selected co-morbidity factor is patient volume and the associated controllable variables include at least one of (i) weight of food consumed being limited, (ii) weight of liquid consumed being limited, (iii) weight of food and liquid consumed being limited, or (iv) amount of food and/or liquid consumed after treatment regulated so that a greater percentage of food and/or liquid is consumed closer to or farther from a next dialysis treatment.

14. The personalized renal failure chronic care system of claim 12, wherein the selected co-morbidity factor is patient blood pressure and the associated controllable variables include at least one of (i) sodium intake being limited, (ii) sodium level of dialysis fluid used during treatment being limited, (iii) fatty foods being limited, or (iv) alcohol consumed being limited.

15. The personalized renal failure chronic care system of claim 12, wherein the selected co-morbidity factor is patient blood sugar and the associated controllable variables include at least one of (i) sugar intake being limited or (ii) dextrose or glucose levels in peritoneal dialysis fluid being limited.

16. The personalized renal failure chronic care system of claim 10, wherein the sensor is a first sensor that is used with the compliance entry feature to confirm that the controllable variable is modified over the testing period as scheduled and a second sensor is used for the evaluation to determine the effect of the controllable variable on the co-morbidity factor relative to the desired value for the co-morbidity factor.

17. The personalized renal failure chronic care system of claim 16, wherein the co-morbidity factor is patient volume, the first sensor includes a weigh scale for food and/or water consumed, and the second sensor includes a weigh scale for weighing the patient.

18. The personalized renal failure chronic care system of claim 16, wherein the co-morbidity factor is patient blood pressure, the first sensor includes a camera for reading sodium levels, and the second sensor includes a blood pressure monitor.

19. The personalized renal failure chronic care system of claim 16, wherein the co-morbidity factor is patient blood sugar, the first sensor includes a camera for reading dextrose or glucose levels, and the second sensor includes a glucose meter.

20. The personalized renal failure chronic care system of claim 1, wherein the software is configured to perform the evaluation only if a level of compliance from the compliance entry feature meets a threshold level.

21. The personalized renal failure chronic care system of claim 1, wherein the overall kidney maintenance plan is analyzed at the server or the HCP data input and output device with at least one other overall kidney maintenance plan to establish at least one preferred controllable variable that consistently shows an ability to maintain or improve kidney disease or kidney functioning levels for a plurality of patients.

22. The personalized renal failure chronic care system of claim 1, wherein at least one of
(i) the patient data input and output device includes a smartphone or a personal computer,
(ii) the HCP data input and output device includes a smartphone or a personal computer,
(iii) the compliance entry feature includes a compliance entry screen displayed by
  (a) the patient data input and output device,
  (b) the HCP data input and output device, or
  (c) a website provided via the network,
(iv) the overall kidney maintenance plan is implemented by the patient using the patient data input and output device, or
(v) the overall kidney maintenance plan is determined at the patient input and output device and delivered to the server or the HCP data input and output device.

23. A personalized renal failure chronic care system for a patient comprising:
a patient data input and output device;
a sensor communicatively coupled to the patient data input and output device and configured to record, as compliance information, at least one of blood pressure data, glucose data, bioimpedance data, heart rate data, movement data, or nutritional data from the patient;
software stored on the patient data input and output device, the software including an automated learning method for creating an overall kidney maintenance plan that specifies one or more controllable variables as actions performed by the patient to prevent or reduce complications associated with chronic kidney disease ("CKD"), the automated learning method configured to present a plurality of controllable variables for selection, wherein the controllable variables for selection include at least one nutritional variable and at least one lifestyle variable, and wherein a selected controllable variable is scheduled to be modified for the patient over a testing period; and
a compliance entry screen displayed by the patient data input and output device, the compliance entry screen configured to receive the compliance information from the sensor, wherein the automated learning method is configured to use the compliance information to confirm that the selected controllable variable was modified over the testing period as scheduled,
wherein the automated learning method is configured to perform an evaluation to determine whether the selected controllable variable is to be included in the overall kidney maintenance plan, the evaluation including
  receiving first evaluation data as a baseline, the first evaluation data related to a chronic kidney disease test of the patient performed during a first time of the testing period,
  receiving second evaluation data that is related to the chronic kidney disease test of the patient performed during a subsequent, second time of the testing period,
  determining from the first evaluation data and the second evaluation data whether a kidney function worsens,
  adding the selected controllable variable as an approved controllable variable to the overall kidney maintenance plan when (i) a worsening of kidney function is not determined between the first evaluation data and the second evaluation data, and (ii) the compliance information provides a confirmation that the selected controllable variable was modified over the testing period,
  omitting the selected controllable variable to from the overall kidney maintenance plan when a worsening is determined between the first evaluation data and the second evaluation data, and
  transmitting the overall kidney maintenance plan to at least one of a server or a health care provider ("HCP") data input and output device over a network,
wherein the software is configured to use the overall kidney maintenance plan including at least one approved controllable variable with the patient data input and output device to implement or control adherence to the overall kidney maintenance plan.

* * * * *